(12) United States Patent
Monassevitch et al.

(10) Patent No.: US 6,884,250 B2
(45) Date of Patent: *Apr. 26, 2005

(54) INTRATUBULAR ANASTOMOSIS APPARATUS

(75) Inventors: Leonid Monassevitch, Givat Olga (IL); Benjamin Spenser, Caesarea (IL); Michael Arad, Tel-Aviv (IL); Ronen Ne'eman, Halfa (IL)

(73) Assignee: NiTi Medical Technologies Ltd., Netanya (IL)

(*) Notice: Subject to any disclaimer, the term of this patent is extended or adjusted under 35 U.S.C. 154(b) by 70 days.

This patent is subject to a terminal disclaimer.

(21) Appl. No.: 10/237,359

(22) Filed: Sep. 9, 2002

(65) Prior Publication Data

US 2004/0015178 A1 Jan. 22, 2004

(30) Foreign Application Priority Data

Jul. 22, 2002 (IL) .................................................. 150855

(51) Int. Cl.⁷ ............................................... A61B 17/08
(52) U.S. Cl. ...................................... 606/153; 606/151
(58) Field of Search ................................ 411/516, 518, 411/543, 909, 530, 53.6; 606/74, 151, 221, 153–155, 157–158, 142, 143, 219, 220; 623/2.36, 2.37, 2.39, 2.4, 2.41

(56) References Cited

U.S. PATENT DOCUMENTS

| | | | |
|---|---|---|---|
| 5,171,252 A | 12/1992 | Friedland | |
| 5,197,648 A | 3/1993 | Gingold | |
| 5,312,024 A | 5/1994 | Grant et al. | |
| 5,344,059 A | 9/1994 | Green et al. | |
| 5,411,508 A | 5/1995 | Bessler et al. | |
| 5,639,008 A | 6/1997 | Gallagher et al. | |
| 5,683,404 A | * 11/1997 | Johnson | 606/151 |
| 6,117,148 A | 9/2000 | Ravo et al. | |
| 6,241,741 B1 | * 6/2001 | Duhaylongsod et al. | 606/153 |
| 6,402,765 B1 | 6/2002 | Monassevitch et al. | |
| 6,425,900 B1 | * 7/2002 | Knodel et al. | 606/139 |
| 2001/0001826 A1 | * 5/2001 | Bolduc et al. | 606/153 |
| 2003/0023251 A1 | * 1/2003 | Gifford et al. | 606/153 |
| 2003/0028205 A1 | * 2/2003 | Vargas et al. | 606/153 |
| 2003/0212418 A1 | * 11/2003 | Yencho et al. | 606/153 |
| 2004/0030348 A1 | * 2/2004 | Peterson et al. | 606/153 |
| 2004/0049212 A1 | * 3/2004 | Whayne | 606/153 |

FOREIGN PATENT DOCUMENTS

EP 0326757 7/1993
SU 1186199 10/1985

* cited by examiner

Primary Examiner—Julian W. Woo
(74) Attorney, Agent, or Firm—Pearne & Gordon LLP

(57) ABSTRACT

An intratubular anastomosis apparatus for joining organ portions of a hollow organ after intussusception which includes an anastomosis ring, and a crimping support element. The anastomosis ring includes a length of a wire formed of a shape memory alloy for crimping adjacent organ portions against the crimping support element so as to cause anastomosis. The anastomosis ring and the shape memory alloy assumes a plastic state, when at a first, lower temperature and an elastic state, when reaching at least a second, higher temperature. The crimping support element provides a support for crimping the organ portions against the support element. Using the anastomosis ring and crimping support element of the present invention reduces the risk of leakage and no staples or sutures remain within the anastomosed organ portion.

8 Claims, 23 Drawing Sheets

US 6,884,250 B2

INTRATUBULAR ANASTOMOSIS APPARATUS

FIELD OF THE INVENTION

The present invention relates, generally to anastomosis and, more specifically, to intratubular anastomosis apparatus

GLOSSARY

Anastomosis: the union of parts or branches (as of streams, blood vessels, or leaf veins) so as to intercommunicate therebetween.

Intussusception: a drawing in of something from without: especially: the slipping of a length of intestine into an adjacent portion.

Proximal: situated close to the user.

Distal: situated distant or away from the user (relative to Proximal).

BACKGROUND OF THE INVENTION

It is known in the art to provide an excision of a segment of diseased colon or intestine as a result, for example, of a perforation, bleeding, inflammation, or tumor and to provide an anastomosis of the cut end portions. This can be conducted by opening the peritoneal cavity or laparoscopically. However, there are two significant problems associated with these procedures.

The integrity of the anastomosis must be sound so that there is no risk of the anastomosis rupturing or leaking into the peritoneal cavity, causing contamination of the clean interior of the peritoneal cavity. Further, opening the bowel and exposing the clean peritoneal cavity to contamination increases the risk of postoperative complications. There have been a number of improvements in the anastomosis procedure over the past decade.

Reference is made to U.S. Pat. No. 5,197,648 to Gingold on Mar. 30, 1993 entitled "Surgical stapling apparatus." There is disclosed an improved circular anastomosis surgical stapling instrument for joining hollow tubular organs. The instrument includes a staple-carrying assembly at its distal end, a centered longitudinally extensible and retractable main shaft centered in the body, and an anvil opposed to the staple-carrying assembly. In a preferred form the end of the main shaft is provided with a plurality of radially extendable arms positioned to overlie the main shaft having spring hinges biasing them radially outwardly away from the main shaft. The instrument also has a second shaft segment in the hollow of the main shaft, which has a conical pointed unit at its distal end.

Reference is also made to U.S. Pat. No. 5,312,024 to Grant, et al. on May 17, 1994 entitled "Surgical anastomosis stapling instrument with flexible support shaft and anvil adjusting mechanism." There is disclosed a stapling instrument for circular anastomosis stapling. The instrument includes a stapling head flexibly mounted by a support shaft to an actuator handle. The support shaft is radially flexible and suitable for insertion into a patient. The flexible support shaft includes a dual coil structure, to be self-supporting in any curved configuration and to resist deflection upon insertion into the patient during actuation of the stapler. The stapling head includes a driver assembly, which is operable to separate staple forming and tissue cutting actions. The actuator handle includes a staple actuator and a cam follower assembly, to facilitate the operation of the instrument by a surgeon. The actuator handle includes a thumb wheel for opening and closing the anvil and an adjusting knob for adjusting the anvil gap. There is also provided a control lever for pivoting the stapling head relative to the flexible support shaft.

Reference is further made to U.S. Pat. No. 5,344,059 to Green, et al. on Sep. 6, 1994 entitled "Surgical apparatus and anvil delivery system therefore." There is disclosed a detachable anvil assembly for use with a circular anastomosis apparatus for tubular organs. This includes an anvil rod with an anvil head mounted on the distal end thereof. The distal end portion is adapted to pivot by about ninety degrees relative to the axis of the rod. A delivery system facilitates delivery of the anvil assembly to the operative site. The pivoting feature of the distal end reduces the transverse profile of the assembly, consequently facilitating introduction and advancement of the anvil assembly into the organ.

Referring, additionally, to U.S. Pat. No. 5,411,508 to Bessler, et al. on May 2, 1995 entitled "Gastrointestinal approximating and tissue attaching device," there is disclosed a steerable intestinal endoscopic stapler. The stapler comprises a circular anvil with a circular stapling anvil surface and a trimming surface, disposed radially inwardly of the stapling surface. A circular stapler drives staples in an array corresponding to the anvil surface and a circular cutting blade operates corresponding to the cutting block. A scope in the hand piece optically connected to a lens in the head assembly is provided for viewing beyond the head assembly. A steering arrangement is provided for steering the head assembly. An activator at the hand piece is for driving staples toward the anvil and for driving the cutting blade toward the cutting block. Tubular tissue ends are joined by staples and excess tissue is trimmed off with the blade.

In addition, reference is made to U.S. Pat. No. 5,639,008 to Gallagher, et al. on Jun. 17, 1997 entitled "Anvil for circular stapler." There is disclosed an anvil for a fastening instrument. The anvil pivots relative to a shaft to facilitate movement of the anvil and instrument. The anvil also has an improved surface for severing tissue and a sloped surface for guiding a knife during use.

In order to avoid opening the bowel and exposing the clean peritoneal cavity, intussusception of the colon or intestine enables the excision to be conducted extra corporeally, that is, outside the body cavity, preventing contamination of the body cavity. There has been a development recently whereby the intussusception, anastomosis and resection of the intussuscepted segment is facilitated.

Reference is made to U.S. Pat. No. 6,117,148 to Ravo, et al. on Sep. 12, 2000 entitled "Intraluminal anastomotic device." There is disclosed a bowel intussusception, anastomosis and severing mechanism for the resected bowel. The device enables these procedures, without exposing the contaminated intraluminal content to the clean abdominal or thoracic cavities. By tying the bowel to a post, which is withdrawn, intussusception is accomplished. Thereafter, anastomosis by stapling and finally intraluminal resection is carried out.

Each of the foregoing inventions utilizes stapling for causing anastomosis of the portions of bowel or intestine to be joined. It would be advantageous to utilize a procedure and apparatus that did not rely on applying a plurality of staples or other connecting devices, which, of necessity, remain in the bowel and which, despite the utmost care by the surgeon, may leak or rupture.

It is known in the art to provide a surgical fastening clip, which applies a clamping force to a site, such as a blood vessel, thereby reducing its cross-sectional area. It is also known to provide a surgical fastening clip formed of a shape memory alloy which deforms to a closed configuration when heated, such that the clamping force applied thereby is increased as it is heated. For example, U.S. Pat. No. 5,171, 252 discloses a surgical fastening clip formed of a shape memory alloy; the device disclosed therein includes separate legs which close tightly around a site. Such a device is limited in its uses, such as for clamping blood vessels, and is not suitable for joining portions of the gastrointestinal tract.

EP 0,326,757 to Fujitsuka Tatsuo Aug. 9, 1999 entitled "Apparatus for anastomosing digestive tract," discloses a device for anastomosing a digestive tract, which includes a plurality of U-shaped retaining clips disposed around a soluble support tube. The tube is positioned inside portions of the digestive tract to be joined, and includes an outer groove around which are disposed the U-shaped retaining clips. The retaining clips are made of a shape memory alloy such that the open ends thereof close at a predetermined temperature, thus joining ends of the digestive tract. Once the ends of the digestive tract have been joined, the tube is dissolved. Such a device is disadvantageous in that its use requires that a plurality of clips to be properly positioned simultaneously. Also, there is no assurance that the resulting junction will be smooth, due to the plurality of sites of the digestive tract joined by the plurality of clips.

SU 1,186,199 to Makarov et al Oct. 23, 1985 entitled "Method Of Making Anastomoses," discloses a memory alloy clip consisting of two parallel coils to be used for joining portions of a hollow organ, such as an organ of the gastrointestinal tract. The portions of the organ to be joined are aligned, and each of the plastic coils is introduced through a puncture formed in the wall of one of the portions. The coils are positioned such that, when heated, they compress the aligned walls therebetween, thus maintaining the portions of the walls held within the loops of the coils adjacent each other. Thereafter, incisions are made through the portions of the walls held within the loops of the coils, such that a passageway is created between the two organ portions. The punctures in the organ walls must then be surgically sewn closed with interrupted surgical sutures.

A major disadvantage of known memory alloy clips is that they permit compression of only approximately 80–85% of the junction perimeter, thus requiring additional manual sutures, which reduce the seal of the junction during the healing period and its elasticity during the post-operative period. Also, this additional suturing is problematic inasmuch as it has to carried out across a joint which includes a portion of the clip, thereby rendering difficult the sealing and anastomosis of the organ portions. Furthermore, once in place, clips according to the prior art require further surgery to be performed, namely, incisions through tissue so as to create a passageway between the two organ portions which have been joined by the clip.

Referring now to U.S. Pat. No. 6,402,765 to Monassezitch et al. on Jun. 11, 2002 for "Surgical Clip", there is recited concerning a surgical clip and method for anastomosing a gastrointestinal tract. The clip is formed at least partly of a shape memory alloy, the clip including: a first length of a wire defining a closed geometrical shape having a central opening; a second length of a wire defining a closed geometrical shape similar in configuration and magnitude to that of the first length of wire, wherein, when placed in side-by-side registration, the first and second lengths of wire fully overlap; an intermediate portion located between the first length of wire and the second length of wire, the intermediate portion formed of a shape memory alloy; a cutting element associated with the first length of wire; a counter element associated with the second length of wire and arranged for cutting engagement with the cutting element; wherein when at a first temperature or higher, the first and second lengths of wire are positioned in a side-by-side closed position and the shape memory alloy is in an elastic state, and further, when at a second temperature or lower, below the first temperature, the shape memory alloy is in a plastic state, thereby enabling the first and second lengths of wire to be moved into and to retain a spaced apart position, and upon heating of the clip to a temperature at least equal to the first temperature, the first and second lengths of wire return to the side-by-side closed position, thereby to apply a compressive force to tissue located therebetween.

Referring further to U.S. application Ser. No. 10/158,673 filed on May 30, 2002, for "Surgical Clip Applicator Device", which is a co-pending continuation-in-part of U.S. Pat. No. 6,402,765 referred to hereinabove, there is disclosed an anastomosis clip applicator device for applying a surgical clip. The surgical clip is formed at least partly of a shape memory alloy, to press together adjacent wall portions of adjacent hollow organ portions so as to effect anastomosis therebetween. The applicator device includes: gripping apparatus for gripping a surgical clip, a release mechanism, associated with the gripping apparatus, and tissue cutting apparatus, operatively associated with the gripping apparatus. There is also apparatus for activating the gripping apparatus, the release mechanism and the cutting apparatus, so as to introduce and apply the surgical clip into adjacent hollow organ portions, such that the surgical clip compresses together the adjacent walls of the hollow organ portions, and thereafter causes the cutting apparatus to perforate the adjacent pressed together organ walls to provide patency through the joined portions of the hollow organ.

The surgical clip and the anastomosis clip applicator device, recited respectively in U.S. Pat. No. 6,402,765 and U.S. application Ser. No. 10/158,673 referred to herein above, relate to a memory alloy clip for insertion through apertures formed in the side-walls of a pair of adjacent hollow organ portions utilizing an anastomosis clip applicator device. Access to the hollow organ is generally extratubular, that is, achieved by means of an open surgery or a laparoscopic procedure during which access to the organ parts results in the risk of exposure of the peritoneal cavity to contamination from the excised organs. Furthermore, the nature of the anastomosis provides a join of the organ portions through the adjacent side-walls; whereas a join formed in the in-line excised ends is generally preferred, specifically avoiding the possibility of a resistance to or reduction in the flow through the anastomosed adjacent organ portions.

There is thus a need for a surgical apparatus which facilitates compression of substantially the entire perimeter of the junction between the organ portions being joined, which would obviate the need for additional manual sutures and which ensures the smooth seal of the junction during the healing period and its elasticity during the post-operative period. Additionally, there is a need for a surgical apparatus, which, once in place, would enable a clear, straight-through passageway to be created between the two organ portions, which have been joined together, without requiring further surgery to be performed on the organ.

SUMMARY OF THE INVENTION

The present invention aims to provide an apparatus for intratubular anastomosis of an hollow organ, which follows excision of an organ portion having, for example, a tumor, inflammation, ulcer or other trauma, by intussusception without exposing the peritoneal cavity to contaminants generally present within such hollow organs. Such a procedure is facilitated with apparatus, which includes elements for intussusception, anastomosis and excision. The diseased organ portion is removed, and the severed ends crimped together using an anastomosis ring formed of a shape memory alloy and a crimping support element, without exposure of the peritoneal cavity to, for example, bowel contaminants. Alternatively, intratubular anastomosis may be similarly achieved following open surgery excision of an organ portion. Initial patency of the gastrointestinal tract is immediately created following both procedures. The anastomosis ring and crimping support element subsequently become detached from the organ when anastomosis is complete and are passed The present invention aims to provide an apparatus for intratubular anastomosis of an hollow organ, which follows excision of an organ portion having, for example, a tumor, inflammation, ulcer or other trauma, by intussusception without exposing the peritoneal cavity to contaminants generally present within such hollow organs. Such a procedure is facilitated with apparatus, which includes elements for intussusception, anastomosis and excision. The diseased organ portion is removed, and the severed ends crimped together using an anastomosis ring formed of a shape memory alloy and a crimping support element, without exposure of the peritoneal cavity to, for example, bowel contaminants. Alternatively, intratubular anastomosis may be similarly achieved following open surgery excision of an organ portion. Initial patency of the gastrointestinal tract is immediately created following both procedures. The anastomosis ring and crimping support element subsequently become detached from the organ when anastomosis is complete and are passed through the bowel.

According to a preferred embodiment of the present invention, there is provided an intratubular anastomosis apparatus for joining organ portions of a hollow organ after intussusception thereof. The apparatus includes an anastomosis ring, and a crimping support element for use therewith, wherein the anastomosis ring includes a length of a wire formed of a shape memory alloy defining a closed generally circular shape, having a central opening, and having overlapping end portions, the anastomosis ring for crimping adjacent organ portions against the crimping support element so as to cause anastomosis therebetween. The anastomosis ring and the shape memory alloy assumes a plastic or malleable state, when at a first, lower temperature and an elastic state, when reaching at least a second, higher temperature. This enables the anastomosis ring to retain a preselected configuration at the first, lower temperature, and an elastic crimping configuration upon reverting to the second, higher temperature. Further, the crimping support element for intratubular insertion provides a support for crimping the organ portions against the support element. The crimping support element has a generally cylindrical side-wall; proximal and distal end walls formed generally transversely to the side-wall, thereby to define therewith the crimping support element; a generally axial aperture for providing flow communication therethrough, and attachment means for operationally engaging the crimping support element to a crimping applicator member so as to position the crimping support element adjacent to the anastomosis ring for facilitating crimping of preselected wall portions of a hollow organ therebetween.

Also in accordance with a preferred embodiment of the present invention, for use with an anastomosis ring, a crimping support element arranged to have intussuscepted organ wall portions crimped thereagainst by the anastomosis ring, so as to cause anastomosis between the wall portions. The anastomosis ring includes a length of a wire formed of a shape memory alloy defining a closed generally circular shape having a central opening and having overlapping end portions, for crimping adjacent intussuscepted organ wall portions, so as to cause anastomosis between the wall portions. The anastomosis ring and the shape memory alloy assumes a plastic or malleable state, when at a first, lower temperature and an elastic state, when reaching at least a second, higher temperature, thereby enabling the anastomosis ring to retain a preselected configuration at the first, lower temperature, and an elastic crimping configuration upon reverting to the second, higher temperature. The crimping support element includes a generally cylindrical side-wall; proximal and distal end walls formed generally transversely to the side-wall, thereby to define therewith the crimping support element; a generally axial aperture for providing flow communication therethrough; and attachment means for operationally engaging the crimping support element to a crimping applicator member so as to position the crimping support element adjacent to the anastomosis ring for facilitating crimping of preselected wall portions of a hollow organ therebetween.

Additionally, in accordance with a preferred embodiment of the present invention, an anastomosis ring, for use with a crimping support element arranged to have intussuscepted organ wall portions crimped thereagainst so as to cause anastomosis between the wall portions. The crimping support element includes a generally cylindrical side-wall, proximal and distal end walls formed generally transversely to the side-wall, thereby to define therewith the crimping support element, a generally axial aperture for providing flow communication therethrough, and attachment means for operationally engaging the crimping support element to a crimping applicator member so as to position the crimping support element adjacent to the anastomosis ring for facilitating crimping of preselected wall portions of a hollow organ therebetween. The anastomosis ring includes a length of a wire formed of a shape memory alloy defining a closed generally circular shape having a central opening and having overlapping end portions, for crimping adjacent intussuscepted organ wall portions, so as to cause anastomosis between the wall portions. The anastomosis ring and the shape memory alloy assumes a plastic or malleable state, when at a first, lower temperature and an elastic state, when reaching at least a second, higher temperature. The anastomosis ring is thereby enabled to retain a preselected configuration at the first, lower temperature, and an elastic crimping configuration upon reverting to the second, higher temperature.

According to a first embodiment of the present invention, the intratubular anastomosis apparatus includes the anastomosis ring and the shape memory alloy which assume a plastic or malleable state, when at a first, lower temperature and an elastic state, when reaching at least a second, higher temperature, thereby enabling the anastomosis ring to retain a preselected configuration at the first, lower temperature, and an elastic crimping configuration upon reverting to the second, higher temperature.

According to a second embodiment of the present invention, the anastomosis ring and the shape memory alloy assume a plastic or malleable state, when at a first, lower temperature and an elastic state, when reaching at least a second, higher temperature, thereby enabling the anastomosis ring to retain a preselected configuration at the first, lower temperature, and an elastic crimping configuration upon reverting to the second, higher temperature.

According to a third embodiment of the present invention, the intratubular anastomosis apparatus including the length of wire is formed having a cross-sectional shape substantially as selected from the group including circular; and elliptical, thereby to control pressure applied to tissue compressed between the anastomosis ring and the crimping support element.

According to a fourth embodiment of the present invention, the anastomosis ring including the length of wire is formed having a cross-sectional shape substantially as selected from the group including circular and elliptical, thereby to control pressure applied to tissue compressed between the anastomosis ring and the crimping support element.

According to a fifth embodiment of the present invention, the intratubular anastomosis apparatus includes the anastomosis ring which is a contracting anastomosis ring at the second higher temperature and which is an expanding anastomosis ring at the second higher temperature.

According to a sixth embodiment of the present invention, the anastomosis ring is a contracting anastomosis ring at the second higher temperature and an expanding anastomosis ring at the second higher temperature.

According to a seventh embodiment of the present invention, the intratubular anastomosis apparatus includes the crimping support element which has an circumferential recess formed in an outer surface thereof for facilitating retaining the contracting anastomosis ring in a predetermined position therein.

According to a eighth embodiment of the present invention, for use with an anastomosis ring, the crimping support element has an circumferential recess formed in an outer surface thereof for facilitating retaining the contracting anastomosis ring in a predetermined position therein.

According to a ninth embodiment of the present invention, the intratubular anastomosis apparatus includes the crimping support element which has an circumferential recess formed in an inner surface thereof for facilitating retaining the expanding anastomosis ring in a predetermined position therein.

According to a tenth embodiment of the present invention, for use with an anastomosis ring, the crimping support element has an circumferential recess formed in an inner surface thereof for facilitating retaining the expanding anastomosis ring in a predetermined position therein.

According to an eleventh embodiment of the present invention, the intratubular anastomosis apparatus includes the crimping support element which is conFigured as a crimping support helix including a length of a wire formed of a shape memory alloy defining a closed generally helical shape, having at least one coil, such that the crimping support helix is an expanding support helix at the second higher temperature.

According to a twelfth embodiment of the present invention, for use with an anastomosis ring, a crimping support element is conFigured as a crimping support helix including a length of a wire formed of a shape memory alloy defining a closed generally helical shape, having at least one coil, such that the crimping support helix is an expanding support helix at the second higher temperature.

According to a variation of the twelfth embodiment of the present invention, the intratubular anastomosis apparatus includes the length of wire which has a cross-sectional shape selected from the list of shapes including circular, square and rectangular.

According to a variation of the thirteenth embodiment of the present invention, for use with an anastomosis ring, the crimping support element includes the length of wire which has a cross-sectional shape selected from the list of shapes including circular, square and rectangular.

According to a fourteenth embodiment of the present invention, the intratubular anastomosis apparatus includes proximal and distal end walls which include one or more proximal and distal lugs, respectively, for facilitating retaining the contracting anastomosis ring in a predetermined position therebetween.

According to a fifteenth embodiment of the present invention, for use with an anastomosis ring, a crimping support element includes proximal and distal end walls which include one or more proximal and distal lugs, respectively, for facilitating retaining the contracting anastomosis ring in a predetermined position therebetween.

BRIEF DESCRIPTION OF THE DRAWINGS

The present invention will be more fully understood and its features and advantages will become apparent to those skilled in the art by reference to the ensuing description, taken in conjunction with the accompanying drawings, in which.

DETAILED DESCRIPTION OF THE INVENTION

The incidence of tumors, ulcers, inflammation and other traumas in the lower large intestine and in other sections of the intestinal tract is significantly high. In order to excise a diseased section of bowel represents a risk of causing contamination to the peritoneal cavity by the discharge from the exposed bowel interior. Also, joining the bowel portions after excising a section of bowel results in a risk of leakage or rupture of the join.

The present invention seeks to provide a solution to both problems by providing apparatus for an improved excision procedure and an improved joining technique. The removal of a troublesome portion of bowel is carried out by intratubular intussusception of that portion. Joining or anastomosis is then accomplished using an intratubular anastomosis apparatus concurrently with the intussusception of the bowel. The preferred fastening apparatus includes an anastomosis ring formed from a shape memory alloy in conjunction with a crimping support element, which become detached from the site when anastomosis is complete. In addition, the preferred fastening apparatus may also be used to achieve anastomosis following conventional or laproscopic excision of a diseased intestinal portion.

Figure 1A:
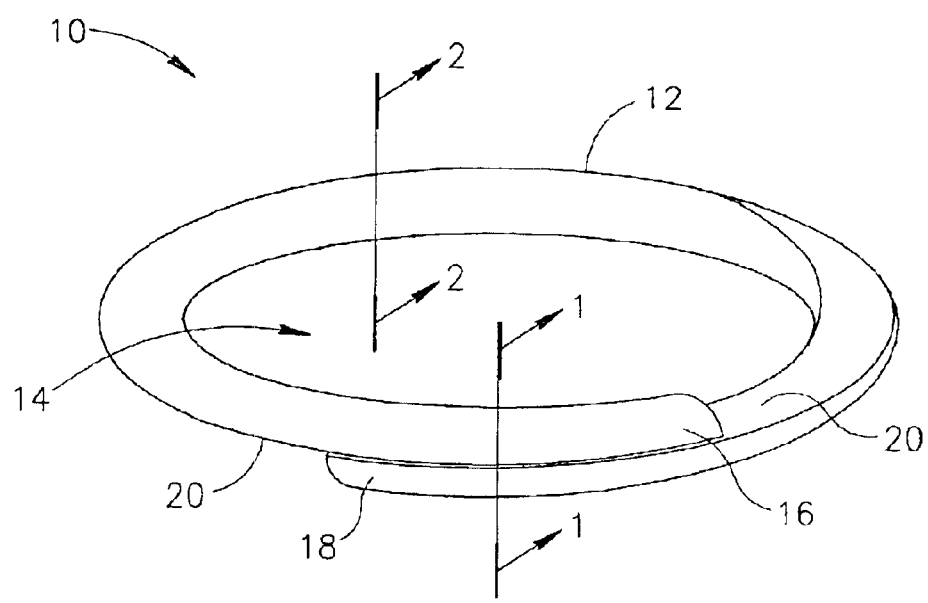
FIG. 1A illustrates a perspective view of an anastomosis ring.

With reference to FIGS. 1A–1D, there is seen, in accordance with a preferred embodiment of the present invention, in FIG. 1A an anastomosis ring generally referenced 10, which is conFigured from a length of shape memory alloy wire 12 as a closed generally circular shaped ring, having a central opening referenced 14, a predetermined wire thickness and overlapping end portions referenced 16 and 18.

Figure 1B:
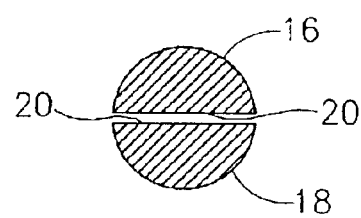
FIG. 1B illustrates a cross-sectional view of overlapping ends of an anastomosis ring as illustrated in FIG. 1A.

In FIG. 1B there is seen a cross-sectional view of overlapping end portions 16 and 18 of anastomosis ring 10 as taken along line 1—1 (FIG. 1A). Each of end portions 16 and 18 has a flat contact surface referenced 20 formed thereon so as to provide a similar cross-sectional profile at overlapping portions 16 and 18 as wire 12.

Figure 1C:
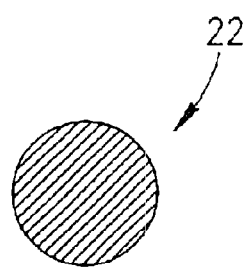
FIGS. 1C and 1D illustrate cross-sectional views of an anastomosis ring as illustrated in FIG. 1A, in accordance with alternative embodiments of the present invention.
Figure 1D:
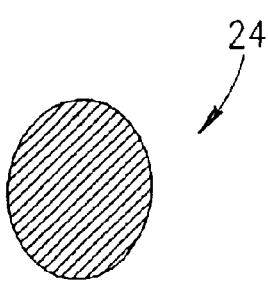

In order to control the pressure on the tissue walls at the point of contact with anastomosis ring 10, the cross-section of the wire forming ring 10 may be varied, in accordance with alternative embodiments of the present invention. In FIGS. 1C and 1D there are seen cross-sectional views, which are non-limiting examples only, of alternative profiles taken along line 2—2 of surgical clip 10 (FIG. 1A). In FIG. 1C there is seen a generally circular cross-sectional profile referenced 22. According to an alternative embodiment of the present invention, there is seen in FIG. 4D an elliptical profile referenced 24.

The shape memory alloy anastomosis ring 10 assumes a plastic or malleable state, when cooled to or below a first, lower temperature and an elastic state, when reaching and exceeding a second, higher temperature. This cooling enables anastomosis ring 10 to retain a malleable configuration at the first, lower temperature. Once the temperature of ring 10 has risen above the transition temperature, ring 10 returns fully to an elastic phase.

Figure 2A:
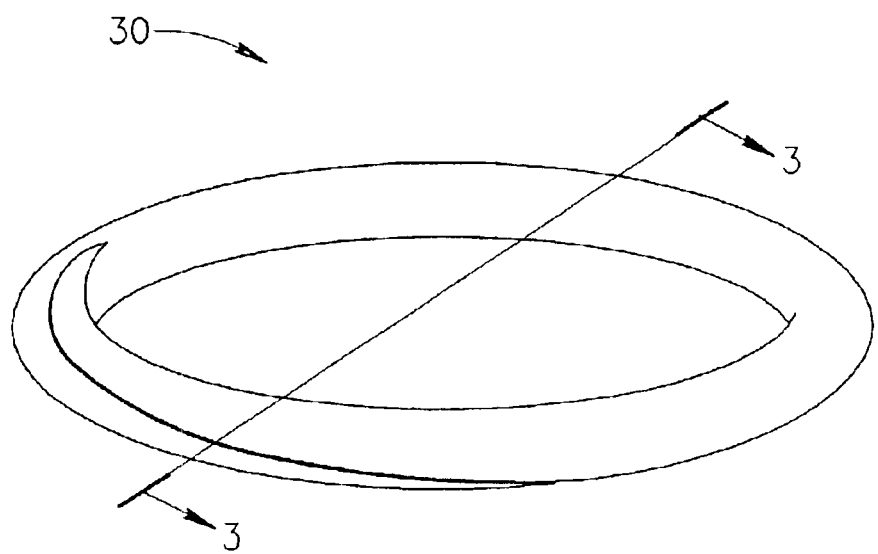
FIG. 2A illustrates a perspective view of an anastomosis ring having a constant circular cross-sectional area.
Figure 2B:
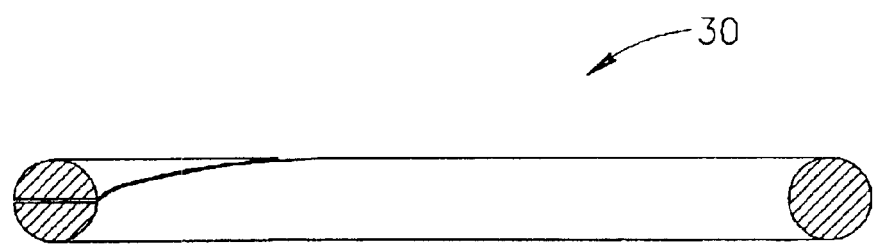
FIG. 2B illustrates a cross-sectional view of the anastomosis ring shown in FIG. 2A.

Referring now to FIG. 2A, there is seen a perspective view of an anastomosis ring generally referenced 30 formed such that the circular cross-sectional area remains constant about the periphery of the ring. A cross-sectional view is seen in FIG. 2B as taken along line 3—3 in FIG. 2A. This constant cross-section ensures that a uniform radial force is exerted as ring 30 contracts or expands.

Figure 3A:
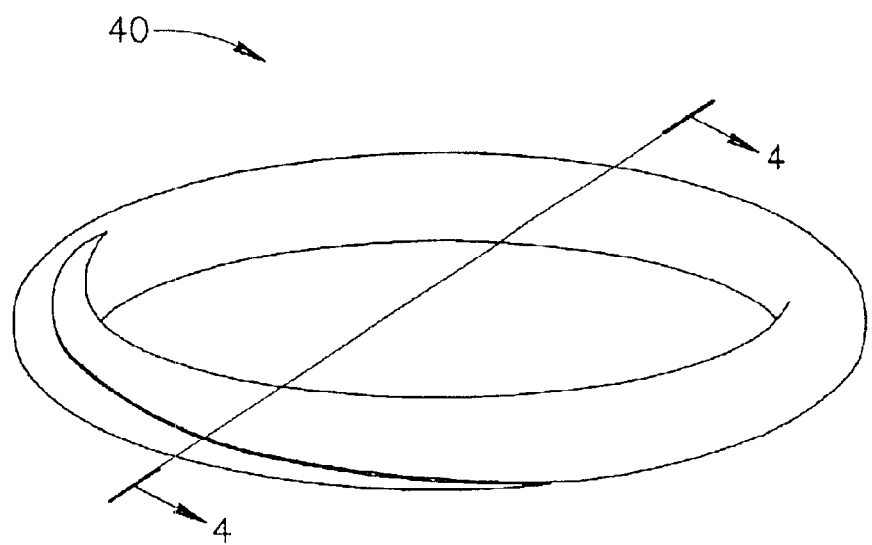
FIG. 3A illustrates a perspective view of an anastomosis ring having a constant elliptical cross-sectional area.
Figure 3B:
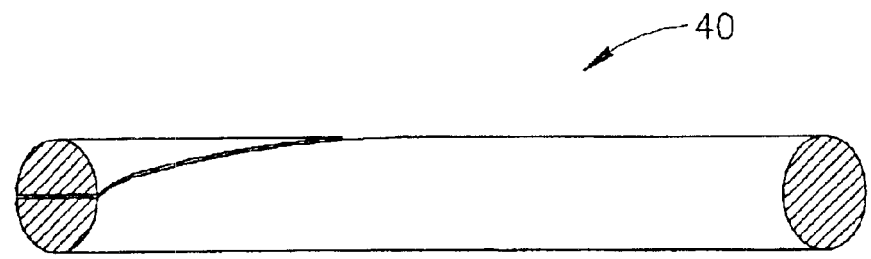
FIG. 3B illustrates a cross-sectional view of the anastomosis ring shown in FIG. 3A.

Referring now to FIGS. 3A and 3B there is seen, respectively, a perspective and a cross-sectional view taken along line 4—4 of an anastomosis ring generally referenced 40, formed such that the elliptical cross-sectional area remains constant about the periphery of the ring, in accordance with an alternative embodiment of the present invention. This ensures that a uniform radial force is exerted as ring 40 contracts or expands. Furthermore, using, for example, various elliptical cross-sections provides a means for controlling the radial pressure exerted by ring 40.

Figure 4A:
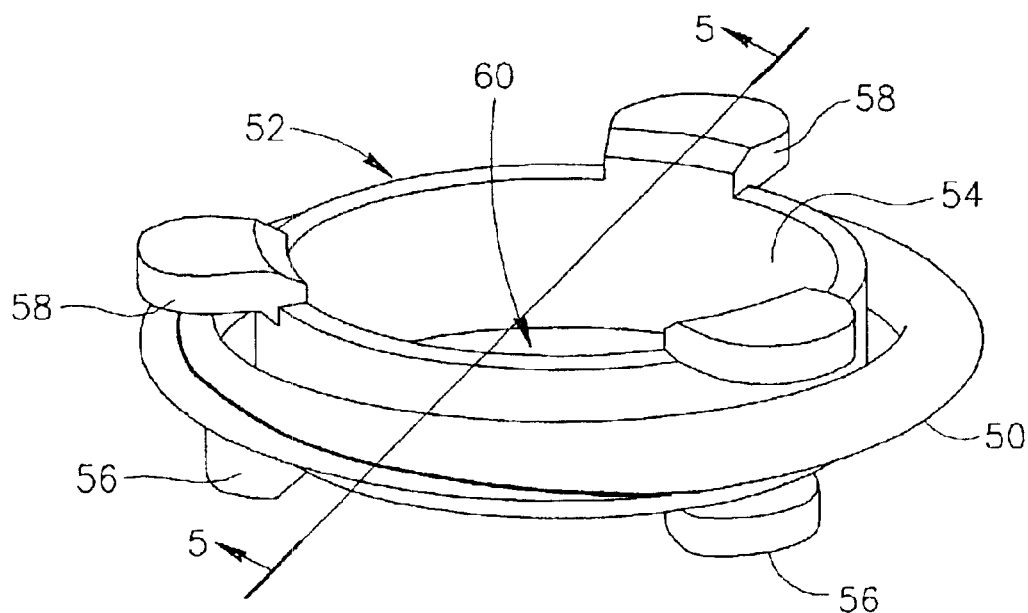
FIG. 4A illustrates a perspective view of an anastomosis ring in crimping engagement with a crimping support element in accordance with a preferred embodiment of the present invention.
Figure 4B:
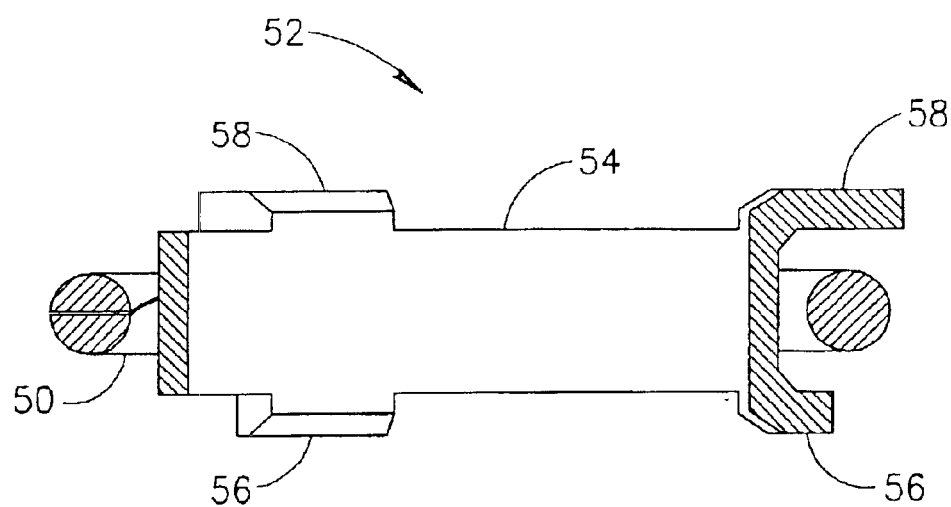
FIG. 4B illustrates a cross-sectional view of the anastomosis ring and crimping support element shown in FIG. 4A.

Referring now to FIGS. 4A and 4B, there is seen, respectively, a perspective and a cross-sectional view of a contractible anastomosis ring referenced 50 in crimping engagement with a crimping support element referenced generally 52, in accordance with a preferred embodiment of the present invention. The cross-sectional view seen in FIG. 4B is taken along line 5-5 in FIG. 4A. Crimping support element 52 includes a short cylindrical section referenced 54, proximal lugs referenced 56 and distal lugs referenced 58 (as disclosed hereinbelow in relation to FIG. 9). Anastomosis ring 50 is caused to contract in position in crimping engagement with organ portions (not shown) against crimping support element 52, as indicated, such that proximal and distal lugs 56 and 58, respectively, ensure that ring 50 remains in position over cylindrical section 54. Crimping support element 52 has an opening referenced 60 to permit passage therethrough.

Figure 5:
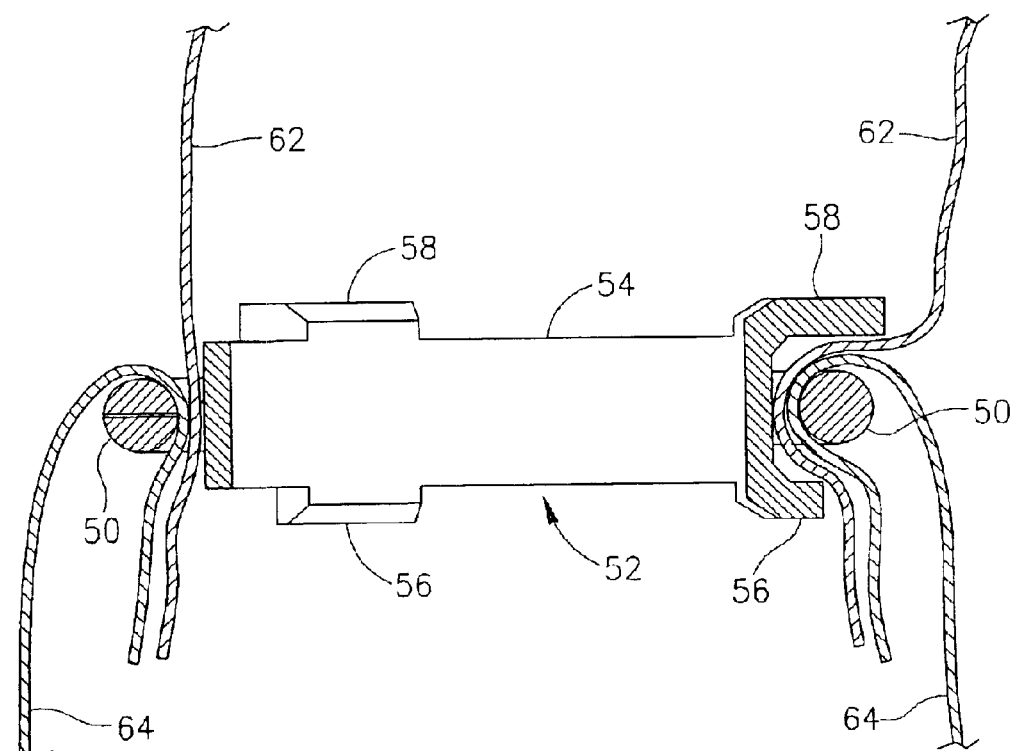
FIG. 5 illustrates a cross-sectional view of the anastomosis ring in crimping engagement with an intussuscepted organ portion and a crimping support element as shown in FIGS. 4A and 4B.

Referring now to FIG. 5, there is seen a cross-sectional view of anastomosis ring 50 in crimping engagement with organ portions referenced 62 and 64 and crimping support element 52 so as to cause anastomosis between the adjacent wall portions 62 and 64, in accordance with a preferred embodiment of the present invention. Crimping of organ portion 62 to portion 64 (as related hereinbelow with reference to FIGS. 16–22) results in anastomosis thereof. Opening 60 (as seen in FIG. 4A) in crimping support element 52 provides immediate patency to anastomosed organ portions 62 and 64.

Figure 6:
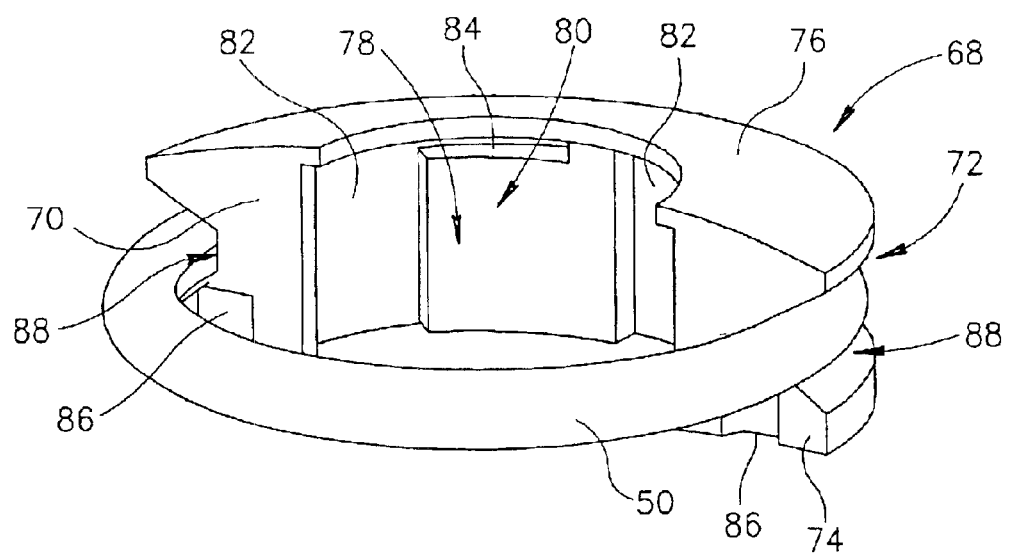
FIG. 6 illustrates a cutaway view of an anastomosis ring in crimping engagement with a crimping support element in accordance with an alternative embodiment of the present invention.

Referring also to FIG. 6, in accordance with an alternative embodiment of the present invention, there is seen a cutaway view of contractible anastomosis ring 50 (as disclosed hereinabove in relation to FIGS. 1A–3B) in crimping engagement with organ portions (not shown) against a crimping support element generally referenced 68. Anastomosis ring 50 is employed to crimp adjacent intussuscepted organ wall portions (not shown, and as related hereinbelow with reference to FIGS. 16–22) against a crimping support element 68 to cause anastomosis thereof. Referring further to FIG. 6, crimping support element 68 has a side-wall referenced 70 defining a generally cylindrical, outward facing surface referenced 72. Crimping support element 68, further has a proximal and a distal end wall referenced 74 and 76 respectively, arranged generally transversely to side-wall 72. A generally axial aperture referenced 78 is formed through crimping support element 68 for providing flow communication therethrough after anastomosis is accomplished by crimping of adjacent organ walls with anastomosis ring 50 thereto (as disclosed hereinbelow in relation to FIGS. 16–22). Axial aperture 78 also defines an inner wall surface referenced 80 of crimping support element 68. Formed in inner wall surface 80 are bayonet engagement recesses referenced 82 and bayonet locking recesses 84. Further, retaining recesses referenced 86 are formed in proximal end wall 74. Formed in outward facing surface 72 is a circumferential recess referenced 88 to ensure precise positioning and retention of contractible anastomosis ring 50 therein.

Figure 7:
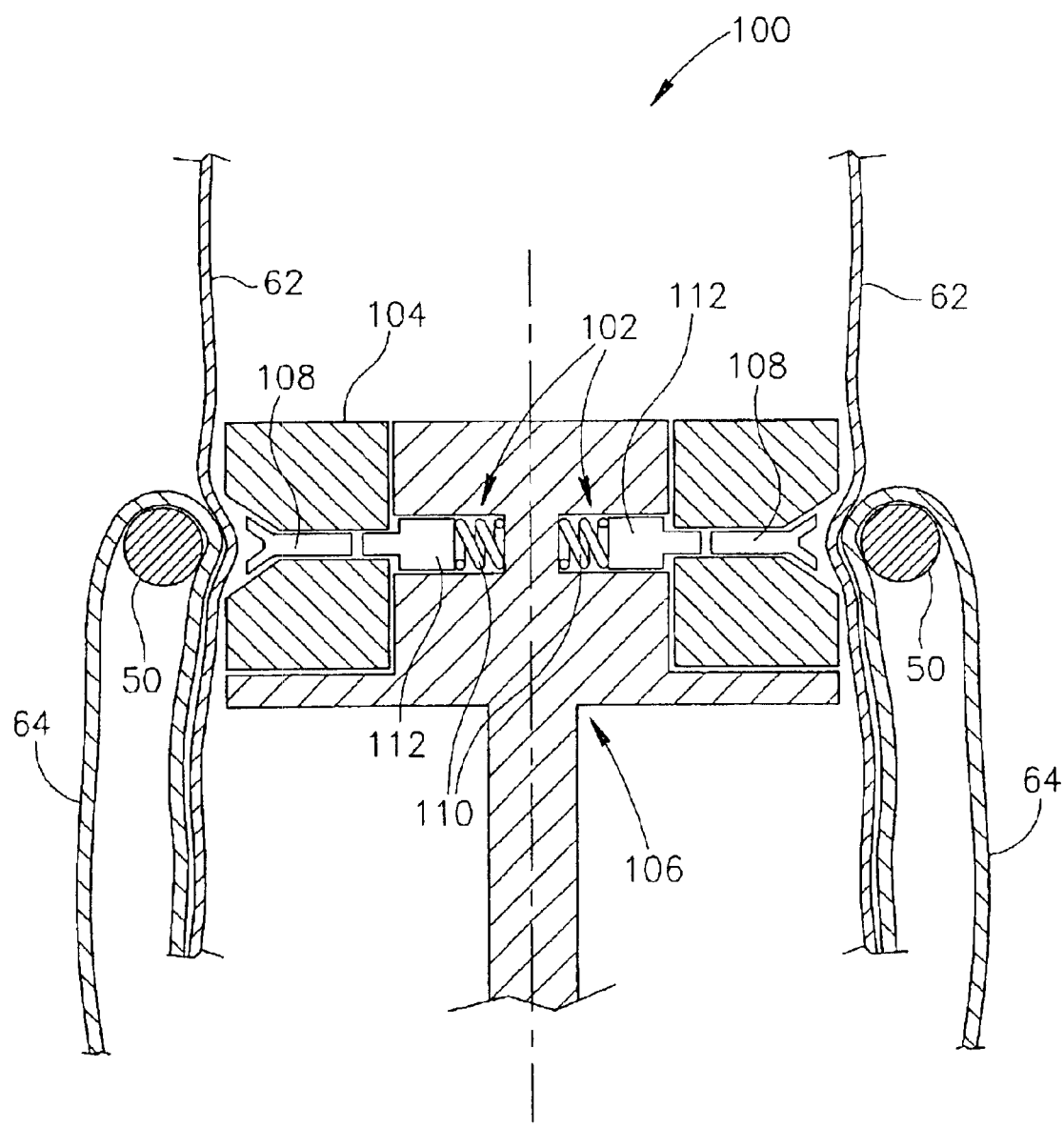
FIG. 7 illustrates a cross-sectional view of a crimping support element release mechanism in accordance with an alternative embodiment of the present invention.

Referring now to FIG. 7, in accordance with an alternative embodiment of the present invention, there is seen a crimping support element generally referenced 100 having a release mechanism generally referenced 102 formed to retain crimping-support element referenced 104 to applicator member referenced 106. Crimping support element 104 is retained in position by retention pins 112, which are kept in a retention mode by springs referenced 110. Further, to release crimping support element 104 from applicator member 106, anastomosis ring 50 is brought into crimping engagement with organ portions 62 and 64 and crimping support element 104. Thereupon, anastomosis ring 50 depresses release pins referenced 108, which, in turn, depress retention pins 112, and thereby cause the release of crimping support element 104 from applicator member 106.

Figure 8A:
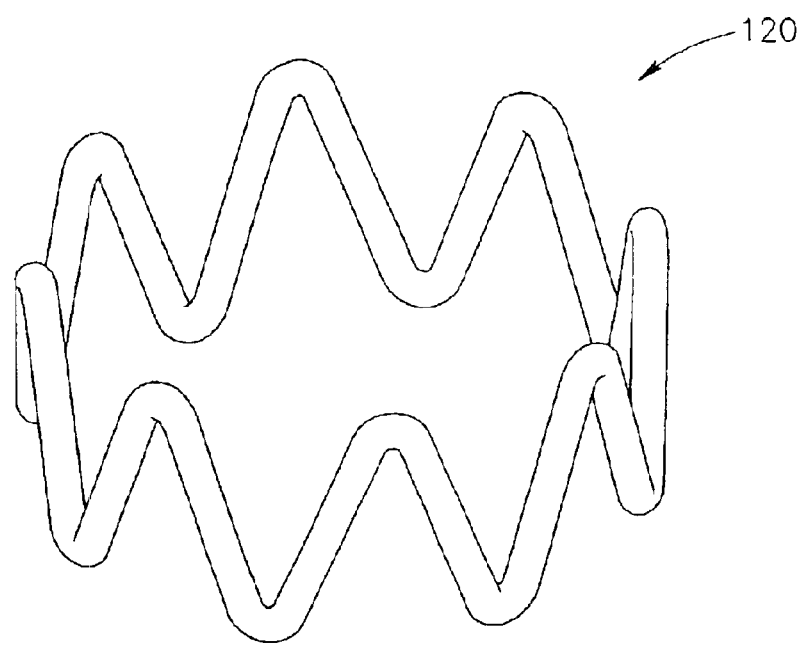
FIG. 8A illustrates a perspective view of an alternative anastomosis ring.
Figure 8B:
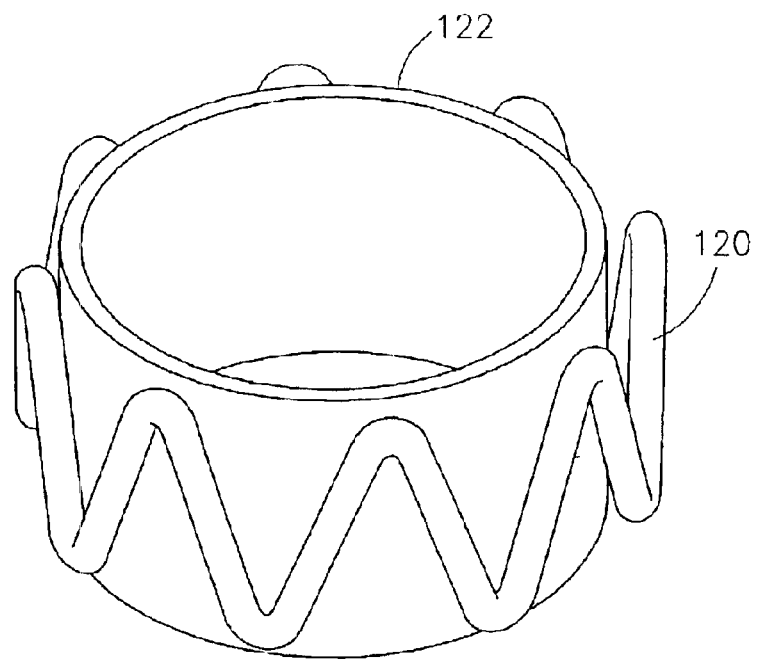
FIG. 8B illustrates the anastomosis ring as shown in FIG. 8A in crimping engagement with a cylindrical crimping support element.

Referring now to FIGS. 8A and 8B, there is seen a perspective view of an alternative anastomosis ring generally referenced 120 having a three-dimensional closed waveform. In FIG. 8B, anastomosis ring 120 is seen in crimping engagement with organ portions (not shown) against a generally cylindrical crimping support element referenced 122. Utilizing an anastomosis ring having, for example, a three-dimensional closed waveform provides a means for controlling and specifically spreading the pressure applied to anastomosed organ portions between ring 120 and crimping support element 122 and for providing a crimping force over a larger surface area, especially when a single coil ring could cause damage to organ portion walls by applying excessive pressure thereto.

With regard to embodiments of the present invention disclosed hereinabove, the relationship between anastomosis ring and crimping support element relates to having a crimping support element within the anastomosed organ walls and a contractible anastomosis ring external to the organ walls. The anastomosis ring is brought into contracting crimping engagement with the organ walls against the exterior surface of the crimping support element. In accordance with additional embodiments of the present invention, an expandable anastomosis ring is disposed within an organ to be anastomosed and brought into crimping engagement with the interior surface of an external crimping support element.

Figure 9:
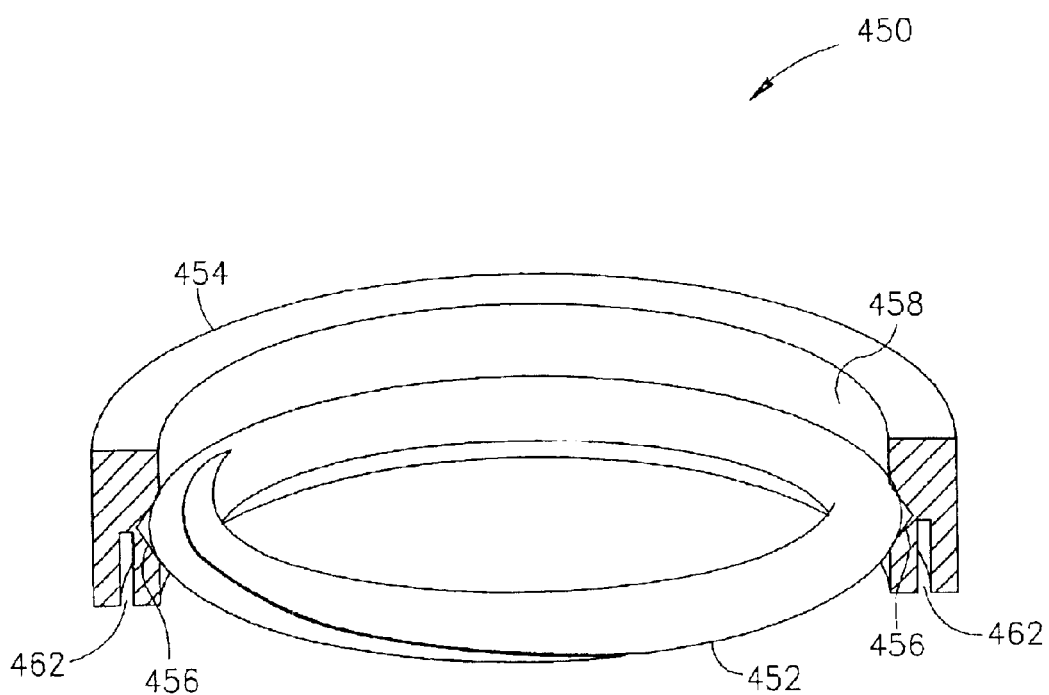
FIG. 9 illustrates a partial cross-sectional view of an expandable anastomosis ring in crimping engagement with an external crimping support element.

Referring now to FIG. 9, there is seen an alternative configuration of an anastomosis apparatus generally referenced 450 including an anastomosis ring referenced 452 in crimping engagement with an organ (not shown) against a generally cylindrical external crimping support element referenced 454. External crimping support element 454 has a retaining recess referenced 456 formed in an interior surface referenced 458 thereof to ensure that anastomosis ring 452 remains engaged therein, and a mounting recess referenced 462 (as disclosed further herein below in relation to FIG. 23).

The consequence of utilizing apparatus 460 (as disclosed further herein below in relation to FIG. 23) together with intratubular expandable anastomosis ring 452 and external crimping support element 454 is the provision of a generally larger aperture formed within the organ at the site of anastomosis compared with that formed when using an internal crimping support member. Nevertheless the aperture is limited by the preselected wall thickness and external diameter of external crimping support element 454. External crimping support element 454 is selected in accordance with the internal diameter of the organ to be treated. Inevitably, an aperture formed at the site of the anastomosis is smaller than the original organ diameter. In order to further increase the anastomosed aperture, in accordance with further embodiments of the present invention, an expandable crimping support element and apparatus for utilizing this expandable crimping support element is disclosed hereinbelow in relation to FIGS. 10–14. Following the crimping of the organ walls using an expandable anastomosis ring against an expandable crimping support element, the aperture formed at the site of anastomosis will be in accordance with the expanded size of the expandable crimping support element.

Figure 10:
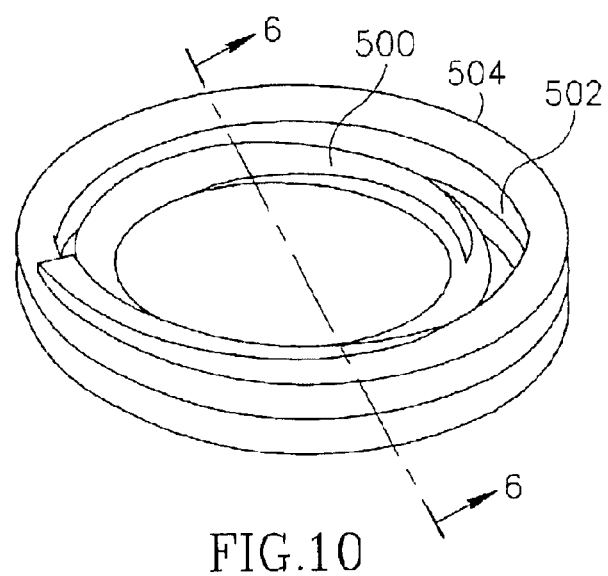
FIG. 10 illustrates a perspective view of an expandable anastomosis ring in crimping engagement with an expandable helix crimping support element in accordance with an alternative embodiment of the present invention.
Figure 11:
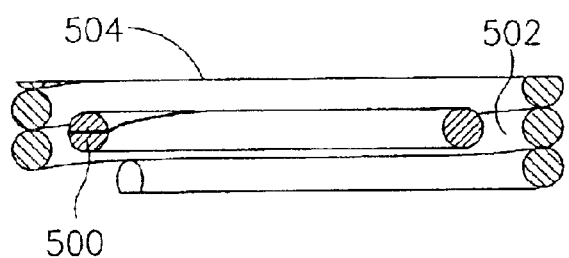
FIG. 11 illustrates a cross-sectional view of the expandable anastomosis ring and expandable helix crimping support element as shown in FIG. 10.
Figure 12:
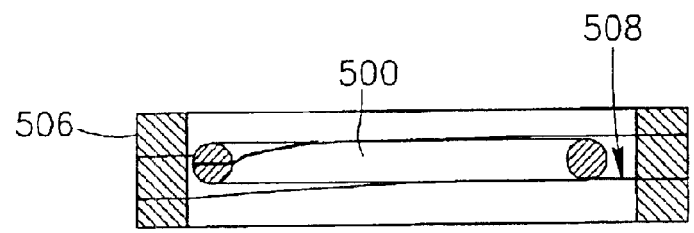
FIG. 12 illustrates a cross-sectional view of the expandable anastomosis ring and an expandable helix crimping support element formed from square section wire generally as shown in FIG. 11 (26)

Referring now to FIGS. 10–12, there is seen an expandable anastomosis ring referenced 500 in crimping engagement with an organ portion (not shown) against an inner face referenced 502 of an expandable helical crimping support element referenced 504 conFigured from a length of substantially circular cross-section memory alloy wire, in accordance with an alternative embodiment of the present invention. In FIG. 11 there is seen a cross-section of expandable anastomosis ring 500 and expandable helical crimping support element 504 taken along line 6—6 in FIG. 10. In FIG. 12 there is seen a cross-section generally as taken along line 6—6 in FIG. 10 of expandable anastomosis ring 500 and an expandable helical crimping support element referenced 506, formed from a generally square section memory alloy wire, thereby forming a generally flatter inner face referenced 508.

Figure 13:
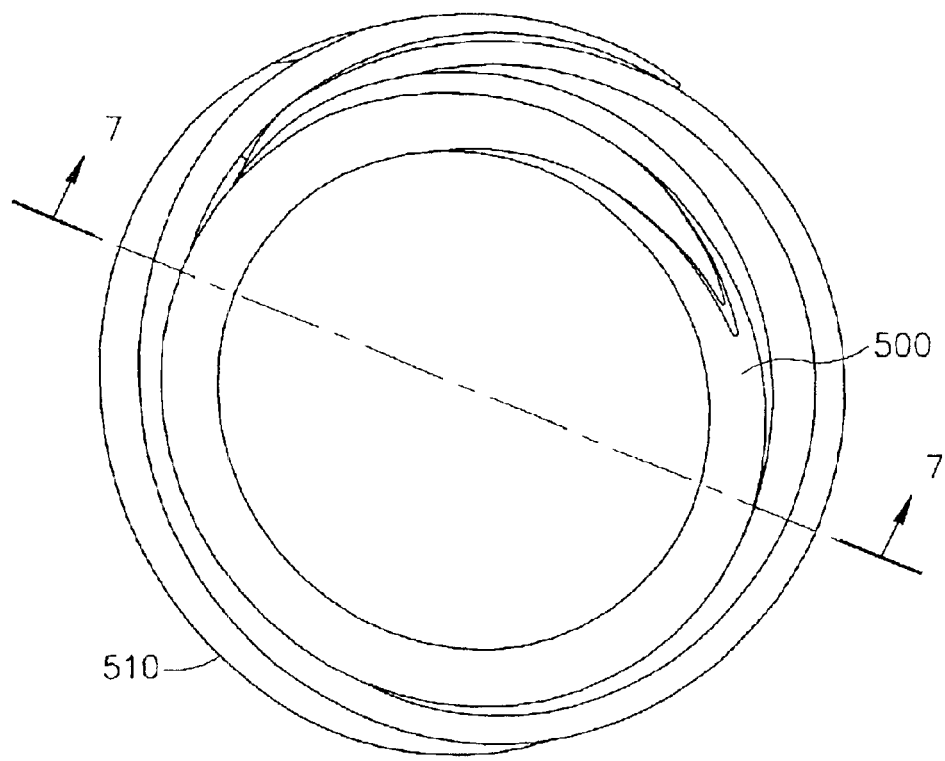
FIG. 13 illustrates a perspective view of an expandable anastomosis ring in crimping engagement with an expandable, coiled, flat-section crimping support element in accordance with another embodiment of the present invention.
Figure 14:
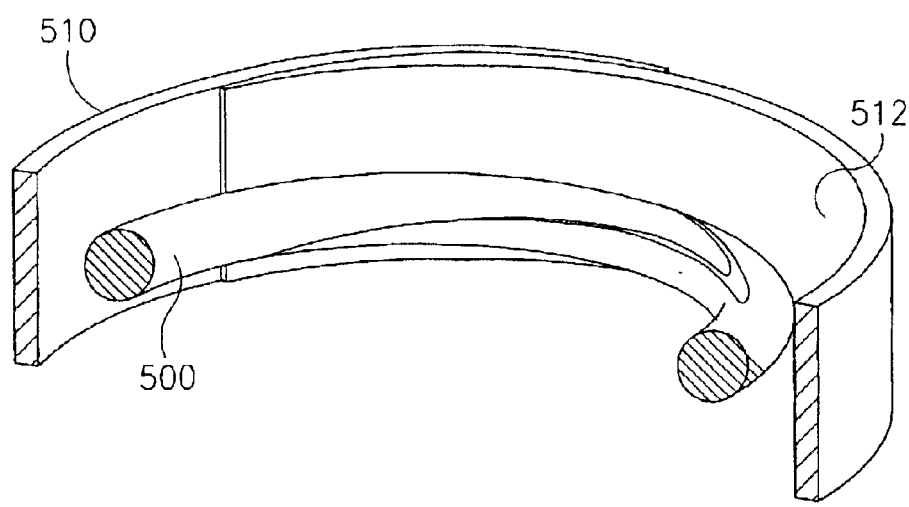
FIG. 14 illustrates a perspective cross-sectional view of the expandable anastomosis ring in crimping engagement with the coiled flat section crimping support element as shown in FIG. 14 (29)

Referring further to FIGS. 13 and 14, in accordance with a variation of an embodiment of the present invention, there is seen expandable anastomosis ring 500 in crimping engagement with organ portions (not shown) against a substantially single coil expandable crimping support element referenced 510. FIG. 13 is a cross-section taken along line 7—7 of FIG. 14. Expandable crimping support element 510 is formed from a substantially flat section strip of memory alloy, having a generally cylindrical configuration and having a generally smooth internal surface referenced 512.

Utilizing apparatus 520 (as disclosed hereinbelow in relation to FIG. 24) together with intratubular expandable anastomosis ring 500 and one of external expandable crimping support elements 504, 506 or 510, a generally larger aperture is formed within the organ at the site of anastomosis, which is not limited by the wire thickness and diameter of external crimping support element 504, 506 or 510. Rather, in accordance with further embodiments of the present invention, the anastomosed aperture is formed in accordance with the expanded diameters of anastomosis ring 500 and of expandable crimping support element 504, 506 or 510.

Apparatus for utilizing a contractible anastomosis ring and crimping support element (as disclosed in relation to FIGS. 1A–8B) is disclosed hereinbelow together with the method for performing an intussusception and anastomosis procedure therewith.

Figure 15:
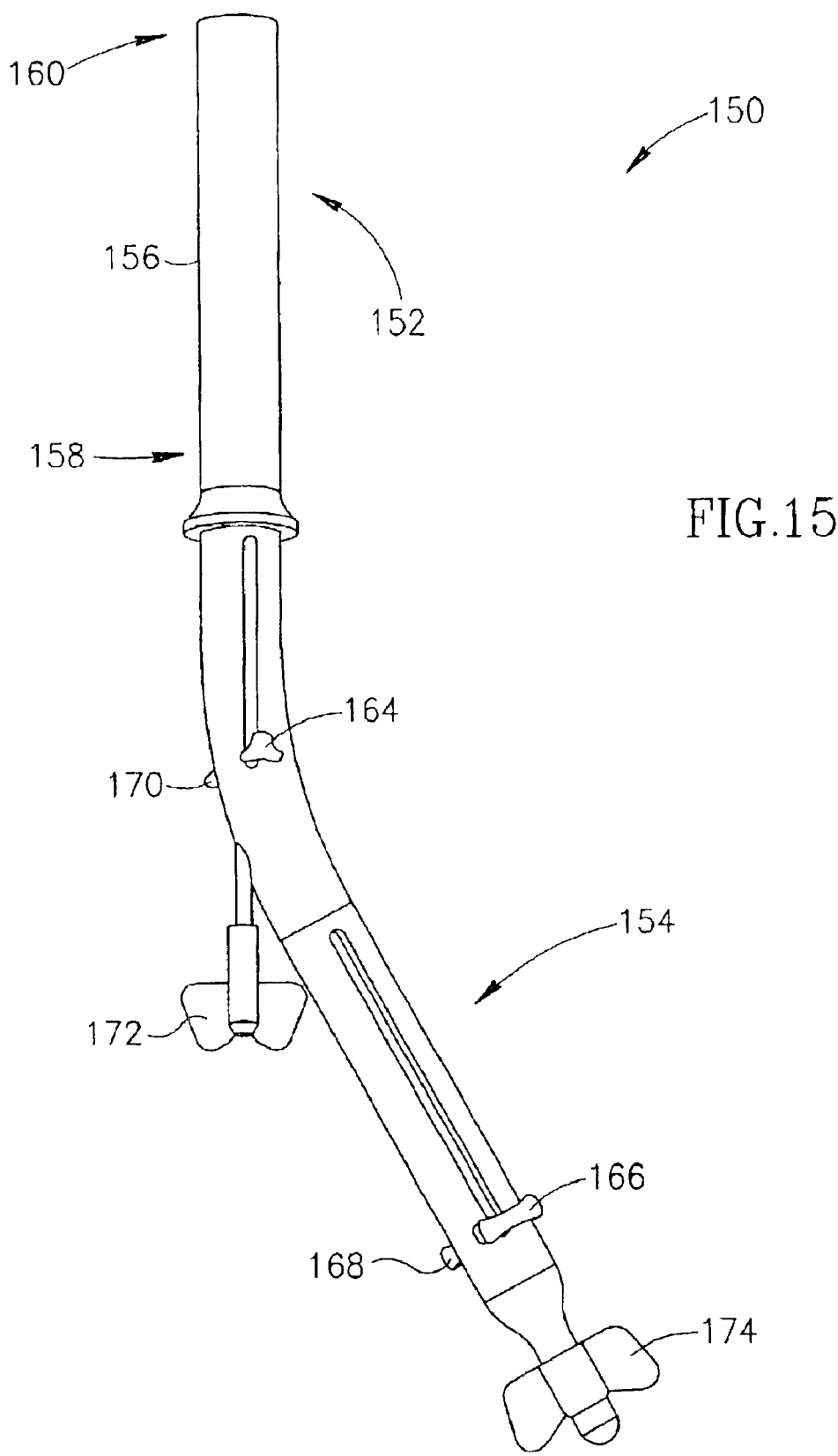
FIG. 15 illustrates an apparatus for intussusception and anastomosis in accordance with an embodiment of the present invention.

Referring now to FIG. 15, there is seen an external view of an apparatus generally referenced 150 for intussusception and anastomosis in accordance with an embodiment of the present invention. Apparatus 150 includes an operative portion referenced generally 152 and a control or activating portion referenced generally 154. Operative portion 152 has an outer cylindrical enclosure referenced 156 having a proximal end generally referenced 158 and a distal end generally referenced 160. Disposed within outer cylindrical enclosure 156 are intussusception and anastomosis apparatus (as referred to hereinbelow in relation to FIGS. 16–22). Control or activating portion 154 includes various control elements to facilitate operation of the intussusception and anastomosis apparatus. The control elements include an anastomosis ring applicator lever referenced 164, proximal and distal clamp jaw levers 166 and 168, respectively, an excising applicator lever referenced 170, crimping support applicator control referenced 172 and intussusception and anastomosis apparatus positioning controller 174. In order to carry out an intussusception and anastomosis, apparatus 150 a user (not shown) grasps control portion 154 and inserts distal end 160 of operative portion 152 a preselected distance into a hollow organ such as the bowel via the anus.

Included with apparatus 150, according to an alternative embodiment of the present invention, there is an optical device (not shown), for providing a view of the interior of the organ being intussuscepted and anastomosed.

With reference to FIGS. 16–22, in accordance with an embodiment of the present invention, there is seen apparatus generally referenced 400 (generally as disclosed hereinabove as operative portion 152 in FIG. 15) for intussusception and anastomosis of a hollow organ generally referenced 402 from which a portion is to be excised. Apparatus 400 has an outer, cylindrical enclosure referenced 412 having a retaining lip referenced 418 formed at the distal end thereof.

Slidably disposed within and coaxial with enclosure 412 is a generally tubular anastomosis ring applicator referenced 420 (FIG. 17), having a recessed portion referenced 424 at the distal extremity thereof, thereby to demountably engage an anastomosis ring referenced 422 thereto (as referred to hereinabove in relation to FIGS. 1A–3B and 8A). Ring applicator 420 is either rigidly or flexibly operatively connected to a control device (not shown) to cause an advancing and retracting movement of ring applicator 420. Ring applicator 420 is advanced to facilitate demountably engaging expanded anastomosis ring 422 thereto while precooled below the transition temperature and in a malleable or plastic state (as disclosed hereinabove in relation to FIGS. 1A–1D). Ring 422 is permitted or caused to warm so as to reach and exceed the transition temperature, thereby reverting to a contractible elastic state. Thereafter, by retracting anastomosis ring applicator 420, anastomosis ring 422 is disengaged from ring applicator recess 424, and is thereby crimps adjacent organ walls 402 against crimping support element referenced 414 which has been pre-aligned with lip 418.

Further, there is seen an intratubular intussusception proximal and distal clamping jaws referenced 404 and 406, respectively disposed coaxially within enclosure 412, for intussusception of a preselected hollow organ portion to be excised from the hollow organ 402. . Clamping jaws 404 and 406 are slidingly operable beyond and retractable within enclosure 412 and anastomosis ring applicator 420. Jaws 404 and 406 are caused to move axially with respect to enclosure 412 to be disposed at a preselected mid-position relative to a diseased organ portion (as referred to hereinbelow). After drawing substantially the mid-portion of the diseased organ portion to within jaws 404 and 406, distal jaw 406 is retractable relative to proximal jaw 404 and, similarly, proximal jaw 404 is advancable relative to distal jaw 406, so as to clamp a preselected organ portion (as disclosed hereinbelow with reference to FIG. 17). Thereafter, intussusception of the preselected organ portion is caused by simultaneously retracting jaws 404 and 406 to within enclosure 412 (as disclosed hereinbelow with reference to FIG. 17).

There is also seen in FIGS. 16–20 a crimping support applicator member generally referenced 425. Crimping support applicator member 425 is configured as a tubular support shaft referenced 428 having a transverse holder referenced 429 formed at the distal end thereof. Crimping support element 414 (as disclosed hereinabove with reference to FIGS. 4A–8B) is demountably fastened to transverse holder 429. Crimping support applicator member 425 has activating means (not shown), which is operationally connected directly or remotely to crimping support applicator member 425 to facilitate advancement or retraction thereof.

According to an alternative embodiment of the present invention, crimping support element 414 (as disclosed hereinabove in relation to FIG. 6), is demountably fastened to an alternatively configured crimping support applicator member, by means of a bayonet fastening mechanism (not shown) formed at a distal end thereof. Bayonet fastening mechanism (not shown) of crimping support applicator member 425 is engaged into bayonet engagement recesses 82 and locked into bayonet locking recesses 84 of crimping support element 68 (seen in FIG. 6), by rotating an inner coaxial shaft (not shown) within tubular support shaft 428. Activating means (not shown) for operating crimping support applicator member 425 is operationally connected directly or remotely to crimping support applicator member 425.

To cause anastomosis ring 422 to crimp organ wall 402 against crimping support element 414, an intratubular anastomosis crimping support element 414 is aligned with lip 418. Thereafter, anastomosis ring 422 (as referred to hereinabove in relation to FIGS. 1A–3B) disengages from anastomosis ring applicator recess 424, and thereby crimps adjacent intussuscepted wall portions of hollow organ 402 against crimping support element 414 (as disclosed hereinbelow with reference to FIGS. 17–18).

Figure 19:
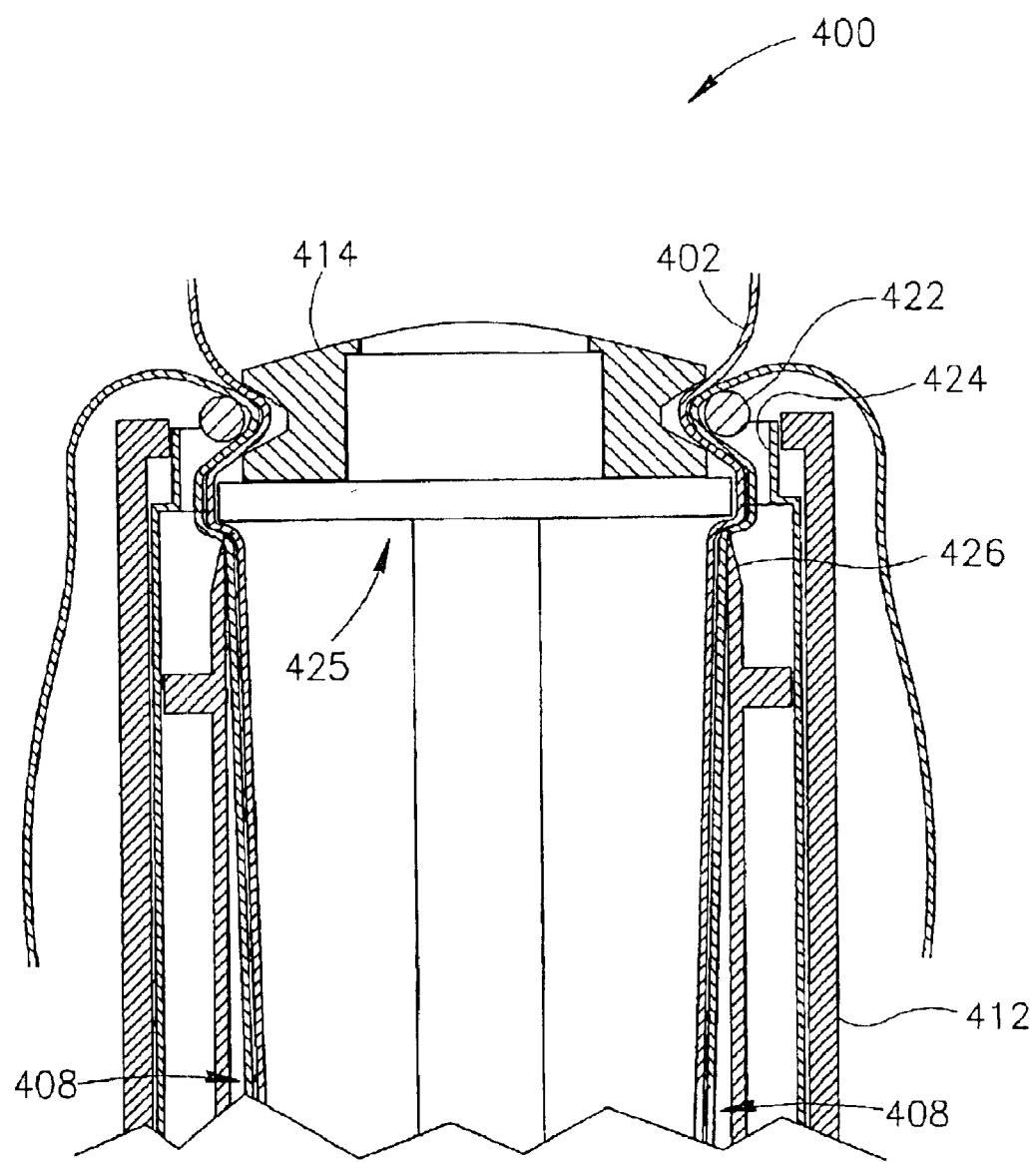
FIG. 19 illustrates a cross-sectional view of a cylindrical cutting blade in cutting engagement with intussuscepted bowel in accordance with a preferred embodiment of the present invention.

In FIGS. 19, there is further seen a cylindrical cutting blade referenced 426, operatively associated with transverse holder 429 of crimping support applicator member 425. Following intratubular intussusception and crimping of the adjacent portions of organ wall 402 with anastomosis ring 422 against crimping support element 414, cylindrical Cutting blade 426 is selectably operable to excise the diseased organ portion. Cylindrical cutting blade 426 is distally advanced towards transverse holder 429 until reaching operative engagement therewith.

Figure 16:
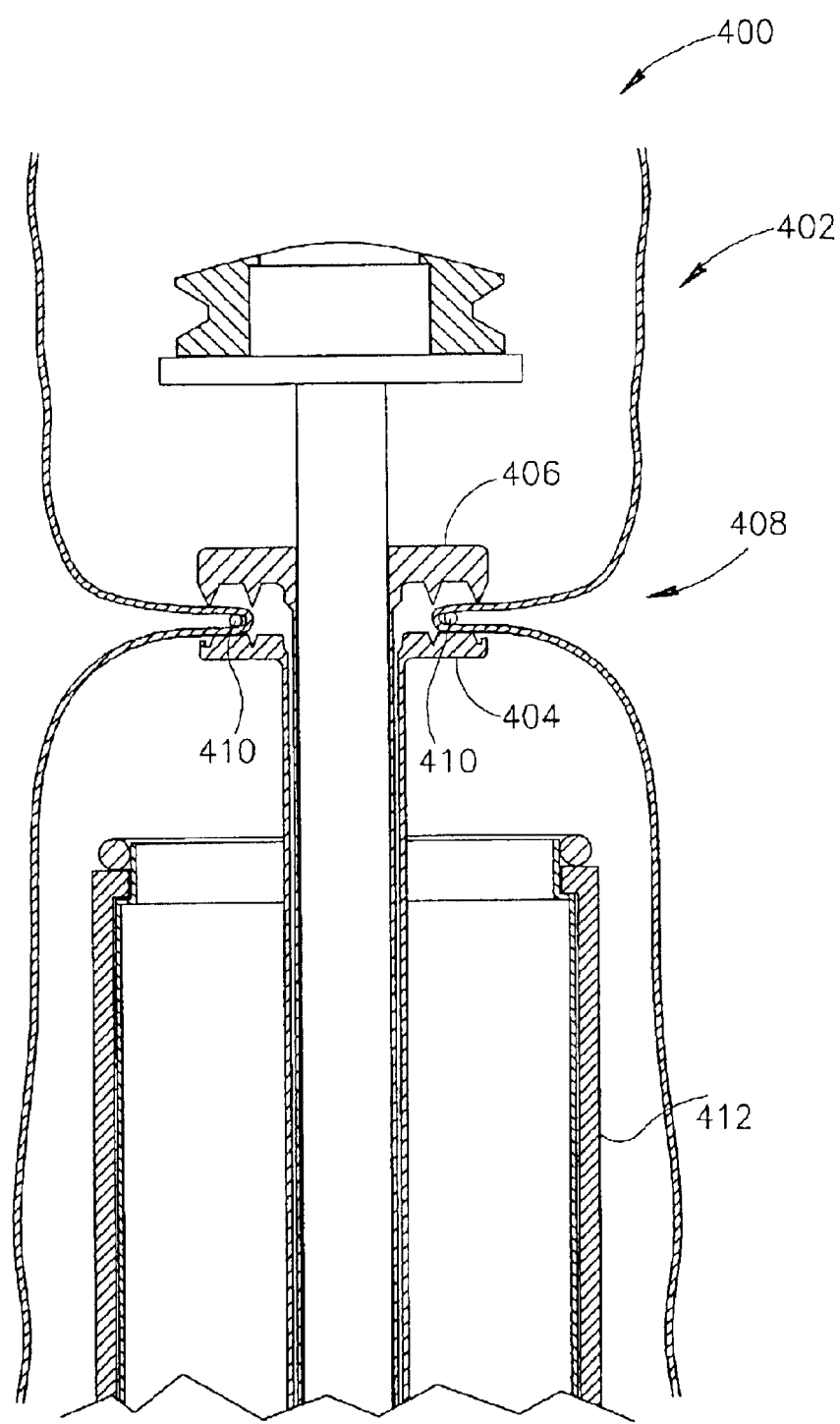
FIG. 16 illustrates a partial cross-sectional view of bowel drawn into clamping jaws prior to intussusception thereof.

Referring now to FIGS. 16–22, the method for performing an intussusception and anastomosis procedure to excise a diseased portion of a hollow organ follows hereinbelow. In FIG. 16 there is seen a cross-sectional view of apparatus generally referenced 400 for intussusception and anastomosis. Apparatus 400 is disposed within a hollow organ generally referenced 402, such that proximal and distal clamp jaws 404 and 406, respectively, are aligned with substantially the middle of organ portion referenced generally 408 to be excised from hollow organ portion 402. Utilizing either Laproscopic or open surgery, substantially the middle of organ portion 408 to be excised is drawn within clamping jaws 404 and 406 by means of an external tie referenced 410. Jaws 404 and 406 are brought into clamping engagement with the drawn in organ portion 408.

Figure 17:
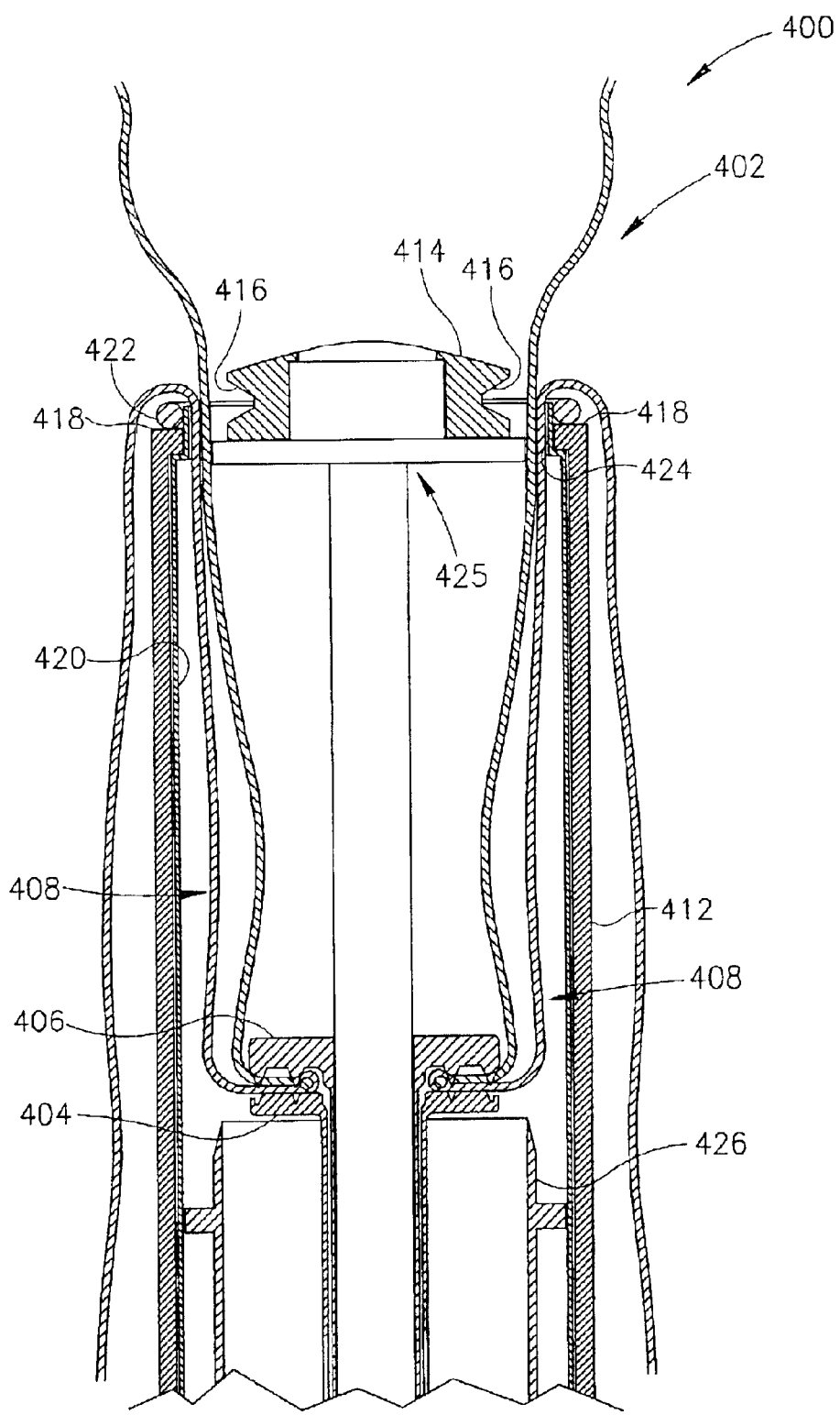
FIG. 17 illustrates a cross-sectional view of an intussuscepted bowel with a crimping support element positioned for crimping.

Thereupon, as seen in FIG. 17, jaws 404 and 406 are simultaneously retracted, while remaining in a clamping engagement, to within enclosure 412, causing intussusception of organ portion 408 of organ 402. Additionally, there is seen, in FIG. 17, crimping support element 414 retracted so as to align circumferential recess 416 therein with the distal lip 418 of enclosure 412.

Figure 18:
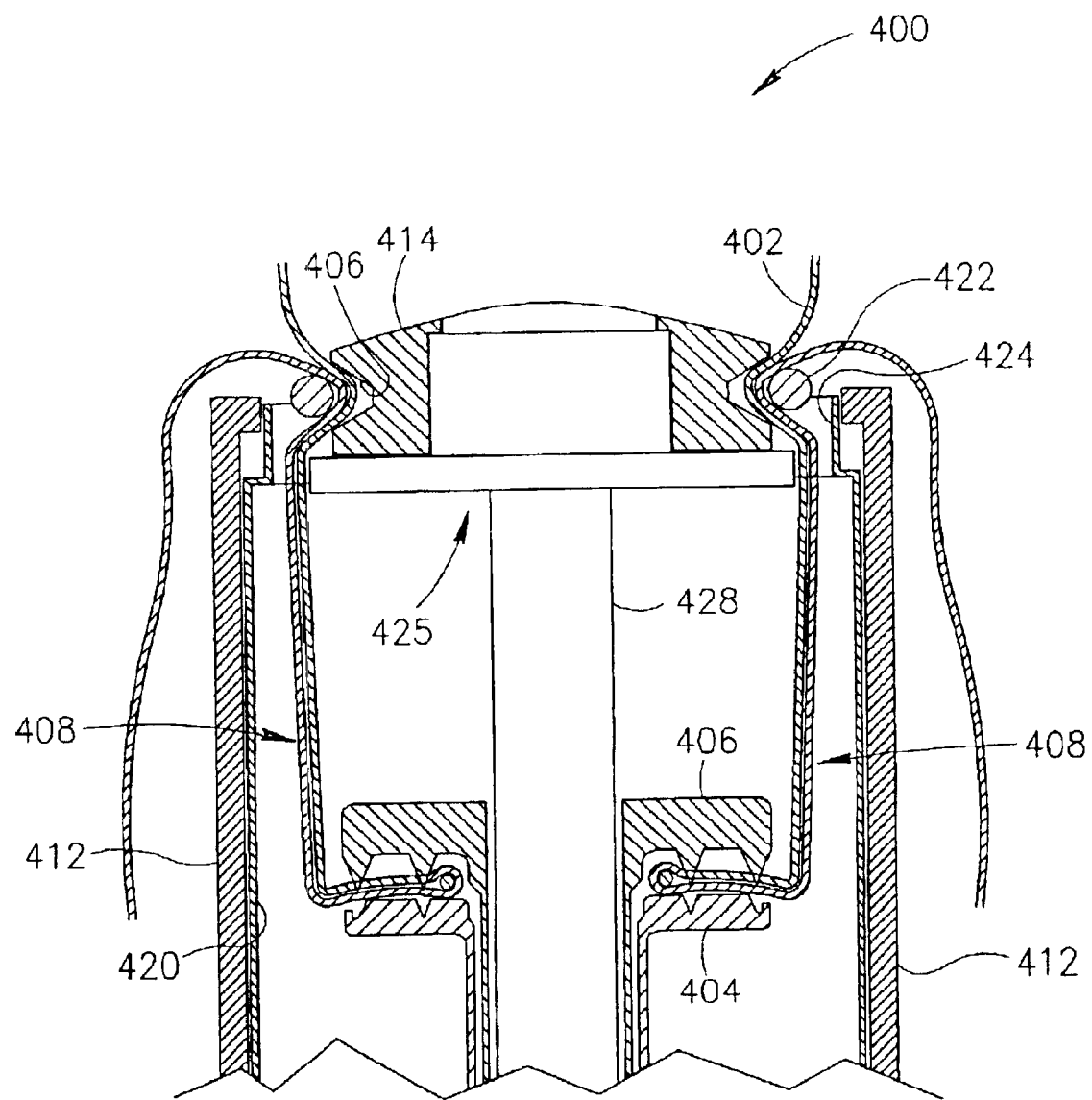
FIG. 18 illustrates a cross-sectional view of an intussuscepted bowel crimped between an anastomosis ring and a crimping support element.
Figure 20:
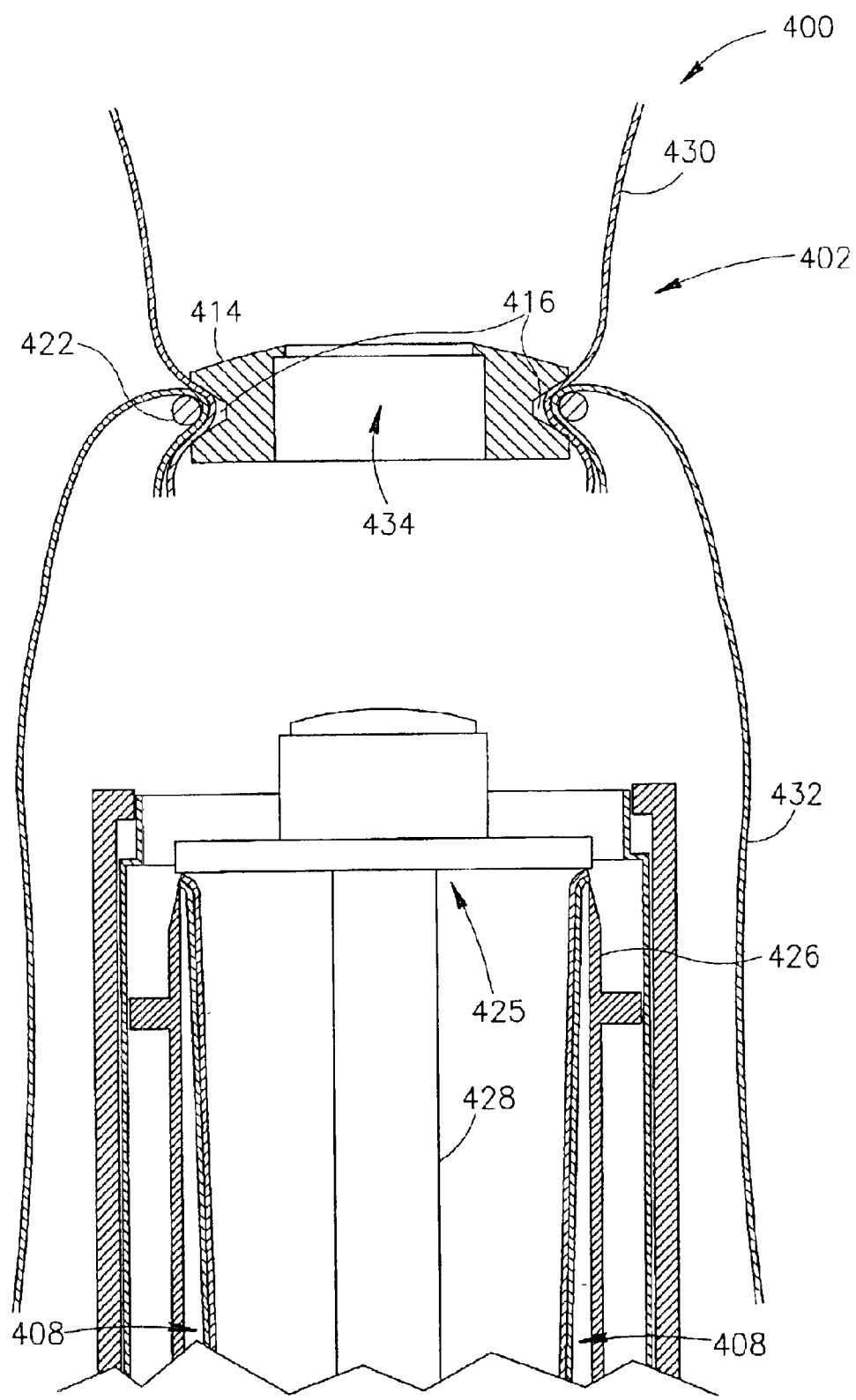
FIG. 20 illustrates a cross-sectional view of the disengaged anastomosis ring and crimping support element joining organ walls.

As seen in FIG. 18, anastomosis ring applicator 420 is slidingly retracted. Thereupon, anastomosis ring 422 is disengaged from ring applicator recess 424 and crimps adjacent organ walls 408 against crimping support element 414 thereby to effect anastomosis of organ 402. As seen in FIG. 19, by advancing cutting blade 426 distally along the axis of apparatus 400 cylindrical cutting blade 426 is brought into cutting engagement with intussuscepted organ wall portion 408. Further, as seen in FIG. 20, apparatus 400 is withdrawn from organ 402, causing anastomosis ring 422 and crimping support element 414 to disengage from crimping support applicator member 425.

According to an alternative embodiment of the present invention, tubular support shaft 428 is rotated thereby to disengage the bayonet fastening mechanism (not shown) formed at a distal end of the alternatively configured crimping Support applicator member 425, from bayonet locking recesses 84 and engagement recesses 82 of crimp support element 68 (as disclosed hereinabove in relation to FIG. 6). Retracting apparatus 400 causes disengagement of crimp support element 414 from crimping support applicator member 425.

Figure 21:
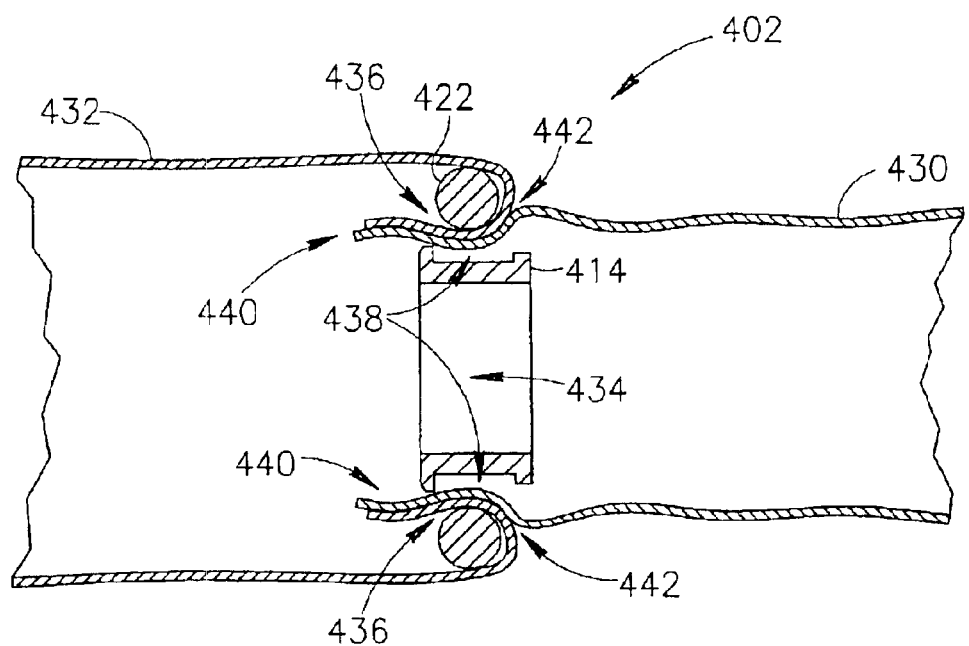
FIG. 21 illustrates a cross-sectional view of an anastomosed bowel with the anastomosis ring and crimping support element providing patency to the bowel.

As seen in FIG. 21, anastomosis ring 422, by crimping adjacent organ portions against crimping support element 414, provides immediate patency to organ 402, bringing portions referenced 430 and 432 of organ 402 into flow communication through axial aperture referenced 434 of crimping support element 414. Organ 402 remains sealed to flow or leakage into the surrounding peritoneal cavity (not shown).

As a result of the pressure exerted by anastomosis ring 422 on wall portions 430 and 432 of organ 402, respective wall areas referenced 436 and 438 are pressed tightly against each other. Blood supply to wall end portions referenced 440 and to areas 436 and 438 ceases, resulting in eventual necrosis of wall areas 436, 438 and 440. While these begin to die-off, wall tissue portions referenced 442, immediately externally adjacent thereto, begin anastomosis such that organ wall portions 430 and 432 of organ 402 become joined, and function as one continuous organ.

Figure 22:
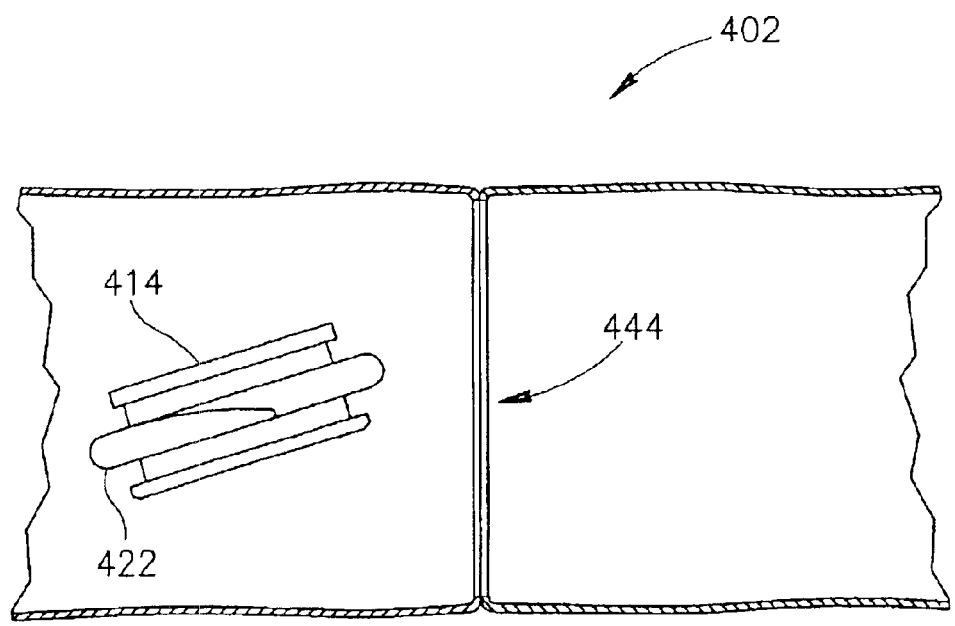
FIG. 22 illustrates a cross-sectional view of anastomosed bowel after the anastomosis ring and crimping support element become detached therefrom.

Once wall areas 436, 438 and 440 becomes fully necrotic, these areas together with anastomosis ring 422 and crimping support element 414 become separated from wall portions 430 and 432, as seen in FIG. 22. This results in an aperture referenced 444 in organ 402 providing little or no restriction to normal organ flow. Necrotic tissue portions 436, 438 and 440 together with anastomosis ring 422 and crimping support element 414 are passed out of organ 402, by normal organ activity.

In accordance with additional; embodiments of the present invention, an expandable anastomosis ring is disposed within an organ to be anastomosed and brought into expandable crimping engagement with an external crimping support element (as disclosed hereinabove in relation to FIG. 9).

Figure 23:
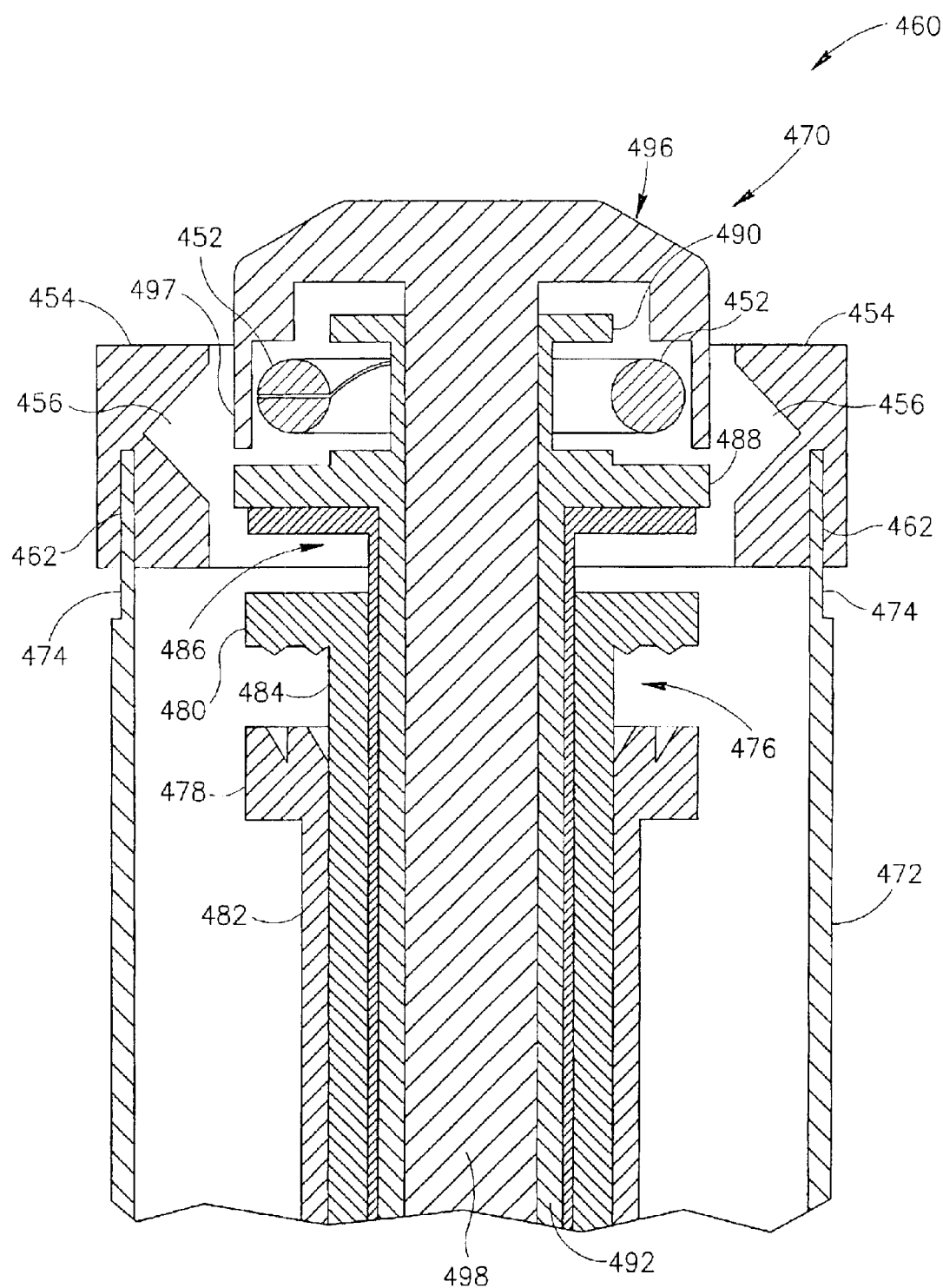
FIG. 23 illustrates an anastomosis release mechanism for applying the expandable anastomosis ring and external crimping support element as shown in FIG. 9.

Referring now to FIG. 23, there is seen an intussusception and anastomosis apparatus, generally referenced 460, including anastomosis apparatus generally referenced 470 for causing anastomosis of portions of a hollow organ (not shown) by bringing an intratubular expandable anastomosis ring referenced 452 into a crimping engagement with organ wall portions (not shown) against external crimping support element 454 (as disclosed hereinabove in relation to in FIG. 9). Crimping support element 454 is demountably attached to cylindrical enclosure referenced 472 by engaging mounting projections referenced 474 thereof into mounting recesses 462 of crimping support element 454. Coaxially disposed within cylindrical enclosure 472 there is seen an intussusception apparatus generally referenced 476 which includes proximal and distal clamping jaws respectively referenced 478 and 480 operatively attached to coaxial tubular clamp operating members respectively referenced 482 and 484 to bring jaws 478 and 480 into clamping engagement with an organ portion (not shown). Further, coaxially disposed within enclosure 472 there is anastoniosis apparatus 470 including an anastomosis ring mounting member referenced generally 486, which includes proximal and distal anastomosis ring holders respectively referenced 488 and 490, axially operable by a coaxial slidingly operable tubular mounting shaft referenced 492.

In order to position expandable anastomosis ring 452 between holders 488 and 490 as indicated, anastoinosis ring 452 is cooled to or below the transition temperature so as to become expandably malleable. Anastomosis ring 452 is malleably disposed on mounting member 486 between holders 488 and 490. To prevent expandable anastomosis ring 452 from expanding away from mounting member 486 as the temperature of anastomosis ring 452 rises to and above the transition temperature, anastomosis ring 452 is restrained by a coaxial ring applicator member generally referenced 496. Anastomosis ring applicator member 496 has an operating shaft referenced 498 coaxially slidingly disposed within tubular mounting shaft 492 and a generally cylindrical ring retaining wall referenced 497. As anastomosis ring 452 warms above the transition temperature, the memory alloy thereof enters the elastic state and expands into engagement with cylindrical retaining wall 497. Apparatus 470 is now ready for use.

After inserting apparatus 460 into an organ portion requiring excision of a diseased portion, intussusception apparatus 476 is caused to clamp a substantially mid-portion thereof (generally as disclosed hereinabove in relation to FIGS. 16–18) and to cause intussusception thereof. Following intussusception, mounting member 486 and applicator member 496 are aligned with recess 456 of crimping support element 454. With mounting member 486 fixed in this position, applicator member 496 is distally advanced, thereby releasing anastomosis ring 452 therefrom, to expand so as to bring organ walls (not shown) into crimping engagement against crimping support element 454. Excision of the intussuscepted organ portion is then carried out (generally as disclosed hereinabove in relation to FIGS. 18–20). Thereafter, withdrawing apparatus 460 from the anastomosed hollow organ causes crimping support element 454 together with anastomosis ring 452 to become detached from mounting projections 474 of apparatus 460.

The consequence of utilizing apparatus 460 together with intratubular expandable anastomosis ring 452 and external crimping support element 454 is the provision of a generally larger aperture formed within the organ at the site of anastomosis. Nevertheless the aperture is limited by the wall thickness and external diameter of external crimping support element 454. An appropriate external support element is selected in accordance with the internal diameter of the organ to be treated. In order to further increase the anastomosed organ aperture, in accordance with further embodiments of the present invention, an expandable crimping support element and apparatus for utilizing this is disclosed hereinbelow in relation to FIG. 24.

Figure 24:
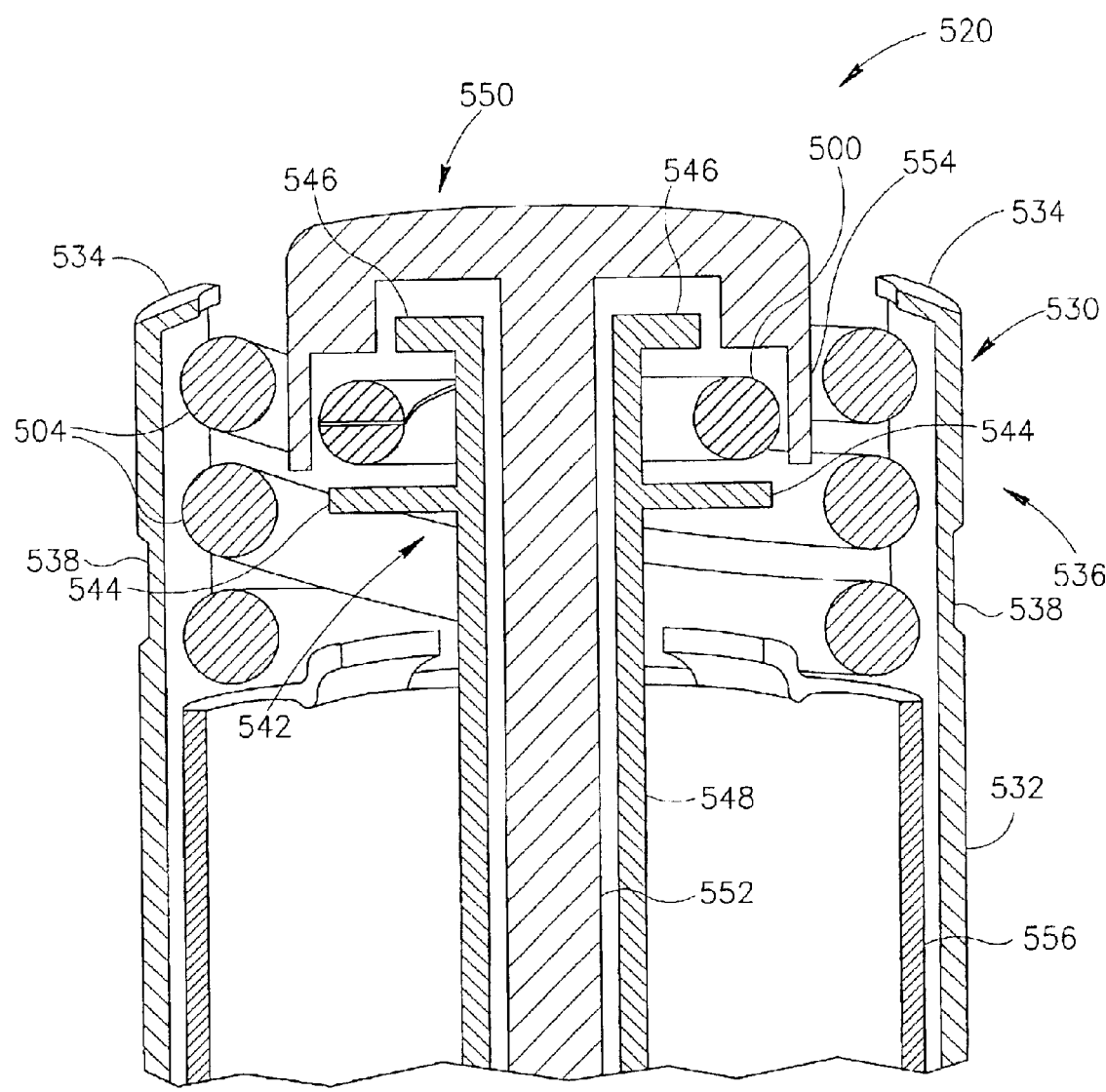
FIG. 24 illustrates an anastomosis mechanism for applying the expandable anastomosis ring and the expandable helix crimping support element as shown in FIGS. 11–15 (26 to 30)

Referring now to FIG. 24 there is seen an intussusception and anastomosis apparatus, generally referenced 520 including anastomosis apparatus generally referenced 530 for causing anastomosis of portions of a hollow organ (not shown) by bringing an intratubular expandable anastomosis ring 500 into crimping engagement with intussuscepted organ wall portions (not shown) against external expandable crimping support element 504.

Crimping support element 504 is cooled below the transition temperature so that the memory alloy thereof becomes malleable thereby allowing crimping support element 504 to be compressed for insertion within retaining collets referenced 534 formed at a distal end 536 of enclosure 532.

Coaxially disposed within cylindrical enclosure 532 are intussusception clamping jaws (not shown; generally as disclosed in relation to FIG. 23). Further, coaxially disposed within enclosure 532 there is anastomosis apparatus 530 including an anastomosis ring mounting member referenced generally 542, which includes proximal and distal anastomosis ring holders respectively referenced 544 and 546, axially operable by a coaxial slidingly operable tubular mounting shaft referenced 548.

In order to position expandable anastomosis ring 500 between holders 544 and 546 as indicated, anastomosis ring 500 is cooled to or below the transition temperature so as to become expandably malleable. Anastomosis ring 500 is malleably disposed on mounting member 542 between holders 544 and 546. To prevent expandable anastomosis ring 500 from expanding away from mounting member 542 as the temperature of anastomosis ring 500 rises to and above the transition temperature, anastomosis ring 500 is restrained by a coaxial anastomosis ring applicator member generally referenced 550. Anastomosis ring applicator member 550 has an applicator operating shaft referenced 552 coaxially slidingly disposed within tubular mounting shaft 548. Applicator member 550 further has a generally cylindrical anastomosis ring retaining wall referenced 554. As anastomosis ring 500, positioned in mounting member 542, warms above the transition temperature, the memory alloy thereof enters the elastic state and expands into engagement with cylindrical retaining wall 554. Apparatus 470 is now ready for use.

After inserting apparatus 520 into an organ (not shown) requiring excision of a diseased portion, intussusception apparatus (not shown) causes intussusception of the diseased organ portion (generally as disclosed hereinabove in relation to FIGS. 16–20). Following intussusception, mounting member 542 and applicator member 550 are generally centrally aligned with crimping support element 504. With mounting member 542 fixed in this position, applicator member 550 is distally advanced, thereby releasing anastomosis ring 500 therefrom, to expand so as to bring organ walls (not shown) into crimping engagement against crimping support element 504. Excision of the intussuscepted organ portion is carried out (generally as disclosed hereinabove in relation to FIGS. 19). Thereafter, disengaging member referenced 556 is distally advanced causing crimping support element 504 together with anastomosis ring 500 to push against and thereby to force collets 534 to flex outwards at recesses 538. Collets 534 are rendered outwardly flexible as a result of recesses referenced 538 formed in an outer face thereof. Crimping support element 504 together with anastomosis ring 500 is thereby detached from apparatus 520 and both crimping support element 504 and anastomosis ring 500 simultaneously expand further to a preselected size.

The consequence of utilizing apparatus 520 together with intratubular expandable anastomosis ring 500 and external expandable crimping support element 504 is the provision of a generally larger aperture formed within the organ at the site of anastomosis. The aperture size is not limited by the wire thickness and external diameter of the unexpanded external crimping support element 504. Rather, in accordance with further embodiments of the present invention, the anastomosed aperture is formed in accordance with the expanded diameters of anastomosis ring 500 and of expandable crimping support element 504.

Figure 25:
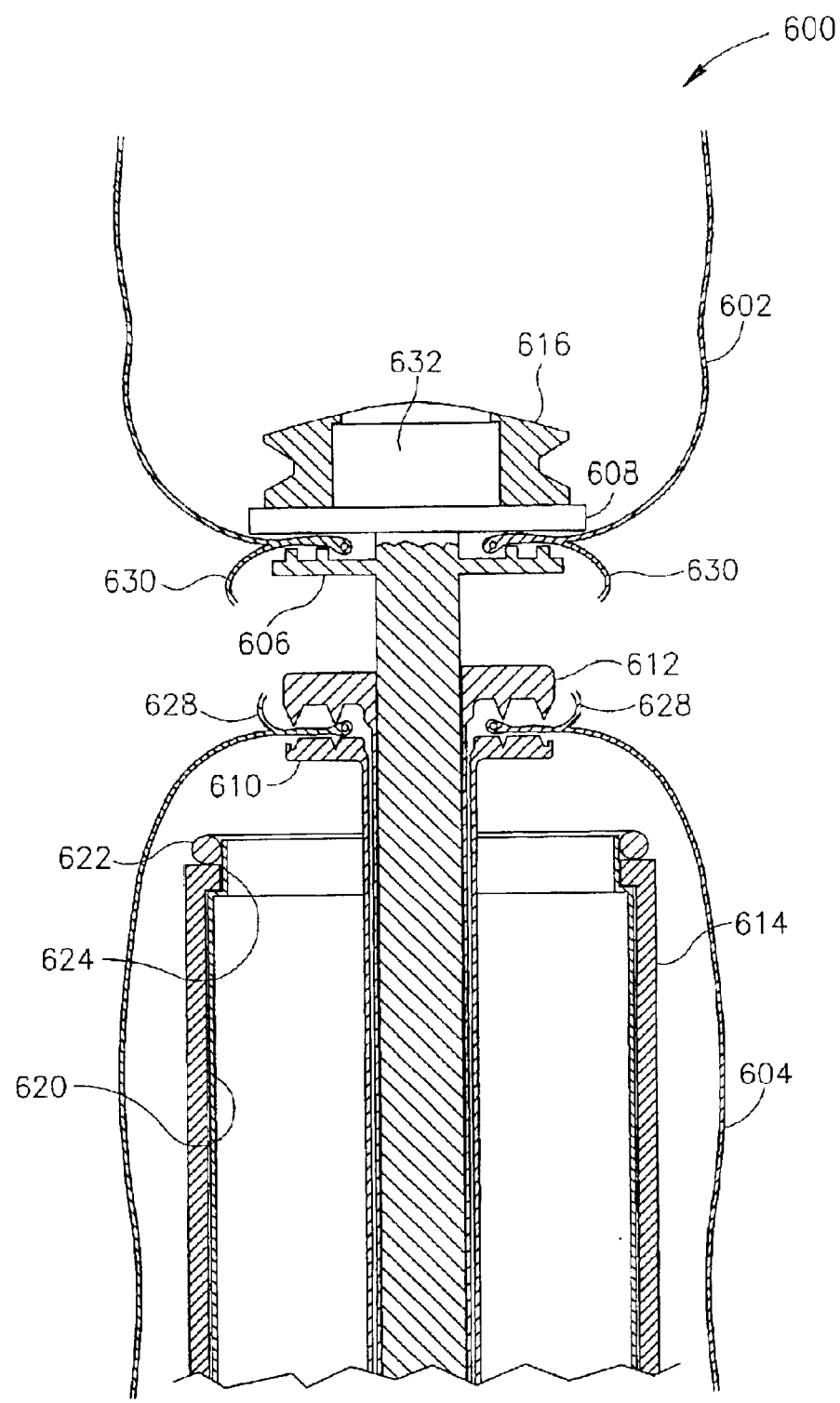
FIG. 25 illustrates surgically excised bowel portions clamped prior to anastomosis in accordance with an alternative embodiment of the present invention.

Under certain circumstances, the surgeon may decide to carry out a conventional, open surgery excising procedure in order to excise a portion of diseased or problematic bowel. The conventional method of joining the bowel portions is utilizing staples or sutures. However, according to an alternative embodiment of the present invention, using an anastomosis ring and a crimping support element, anastomosis is achieved whereby the risk of leakage is substantially reduced and no staples or sutures remain in the anastomosed bowel. Referring now to FIG. 25 there is seen a modified intussusception and anastomosis apparatus generally referenced 600, inserted into organ portion referenced 604, clamping surgically excised bowel portions referenced 602 and 604. The intussusception and anastomosis apparatus (as disclosed hereinabove in relation to FIGS. 16–21), is modified, in so far as an additional clamping jaw referenced 606 is disposed immediately proximate to transverse crimping support applicator 608 to facilitate clamping surgically excised organ portion 602 therebetween. Organ portion 604 is clamped between jaws referenced 610 and 612.

Figure 26:
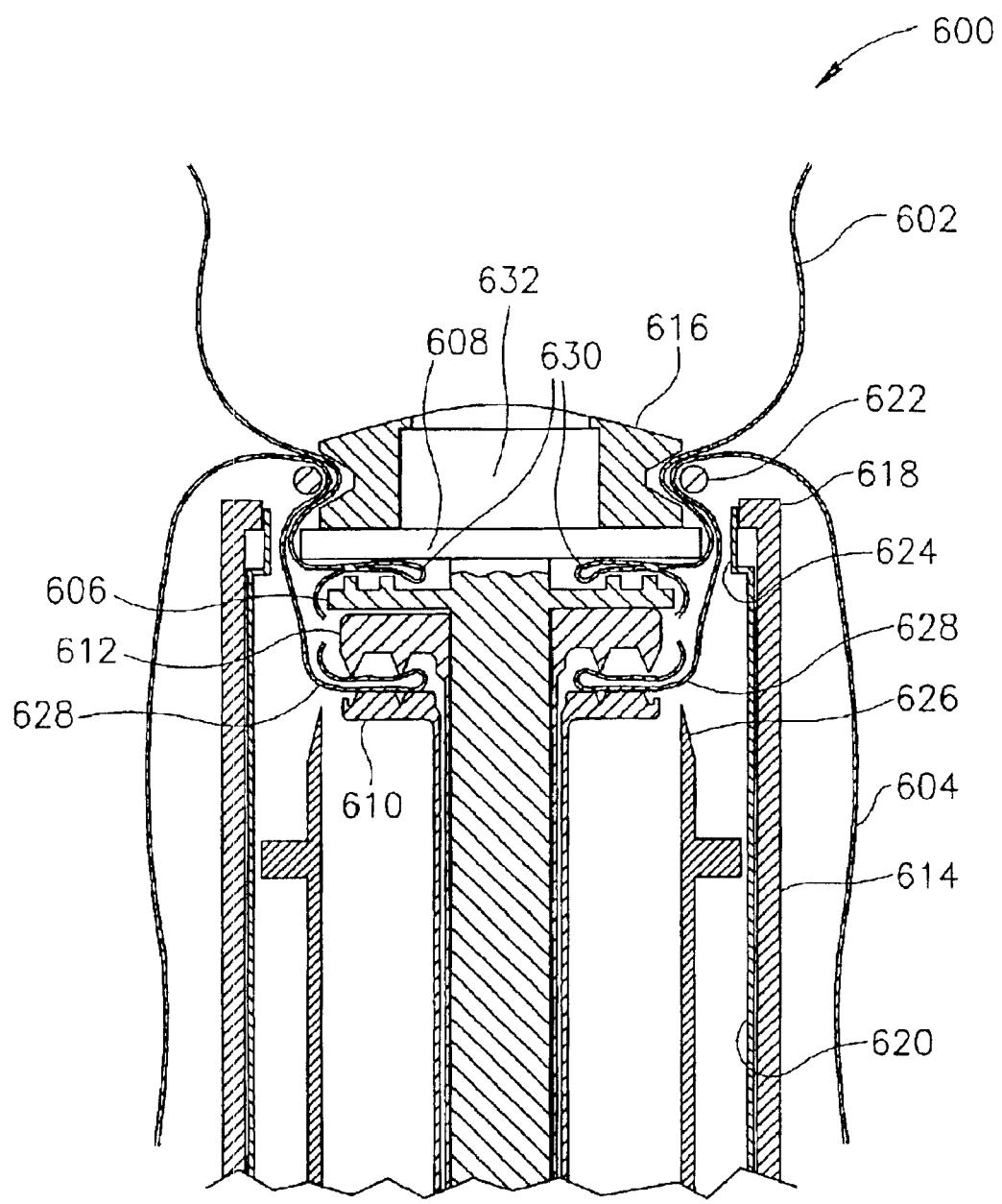
FIG. 26 illustrates a crimped surgically excised bowel portions with a cylindrical cutting blade positioned prior to cutting engagement therewith.

Referring now to FIG. 26, clamped organ portions 602 and 604 are partially intussuscepted by simultaneously retracting clamping jaws 610 and 612 in clamping engagement with organ portion 604 into enclosure 614 and thereafter simultaneously retracting transverse crimping support applicator 608 and clamping jaw 606 in clamping engagement with organ portion 602. Both pairs of clamping jaws, 606 and 608 and 610 and 612 are further retracted to cause crimping support element 616 to be aligned with lip 618 of enclosure 614. Anastomosis ring applicator referenced 620 is then retracted so as to release anastomosis ring 622 from recess referenced 624 thereby to crimp organ portions 602 and 604 against crimping support element 616. Cylindrical cutting blade referenced 626 is distally advanced to provide cutting engagement with crimped organ portions 602 and 604 against transverse crimping support applicator 608 to excise clamped portions referenced 628 and 630 therefrom. Thereafter crimping support element 616 and anastomosis ring 622 are disengaged from crimping support applicator generally referenced 632 (as disclosed hereinabove in relation to FIGS. 19–22) to provide patency to anastomosed organ portions 602 and 604.

Figure 27:
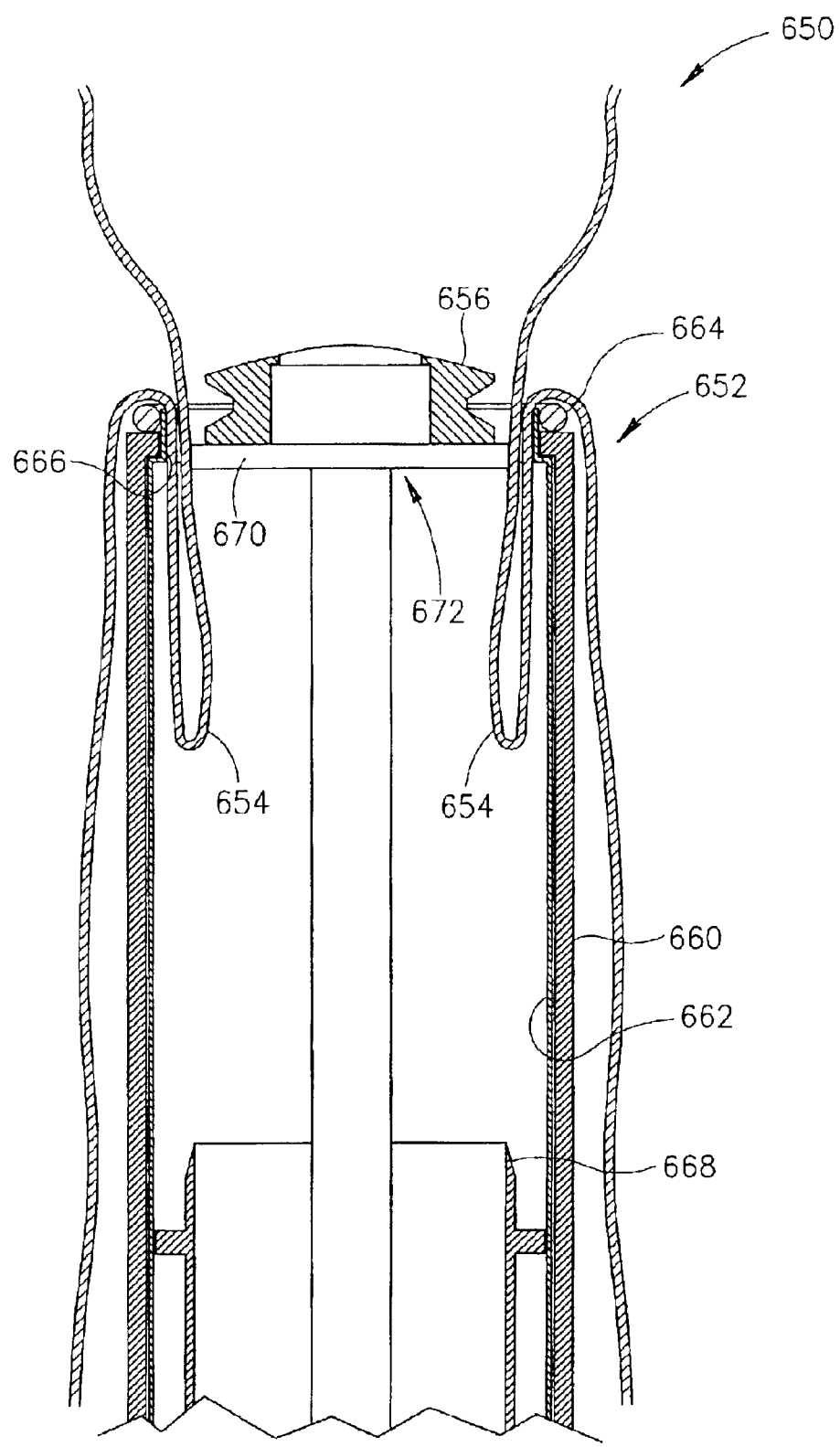
FIG. 27 illustrates a cross-sectional view of a crimping support element positioned prior to crimping of a prolapsed bowel.
Figure 28:
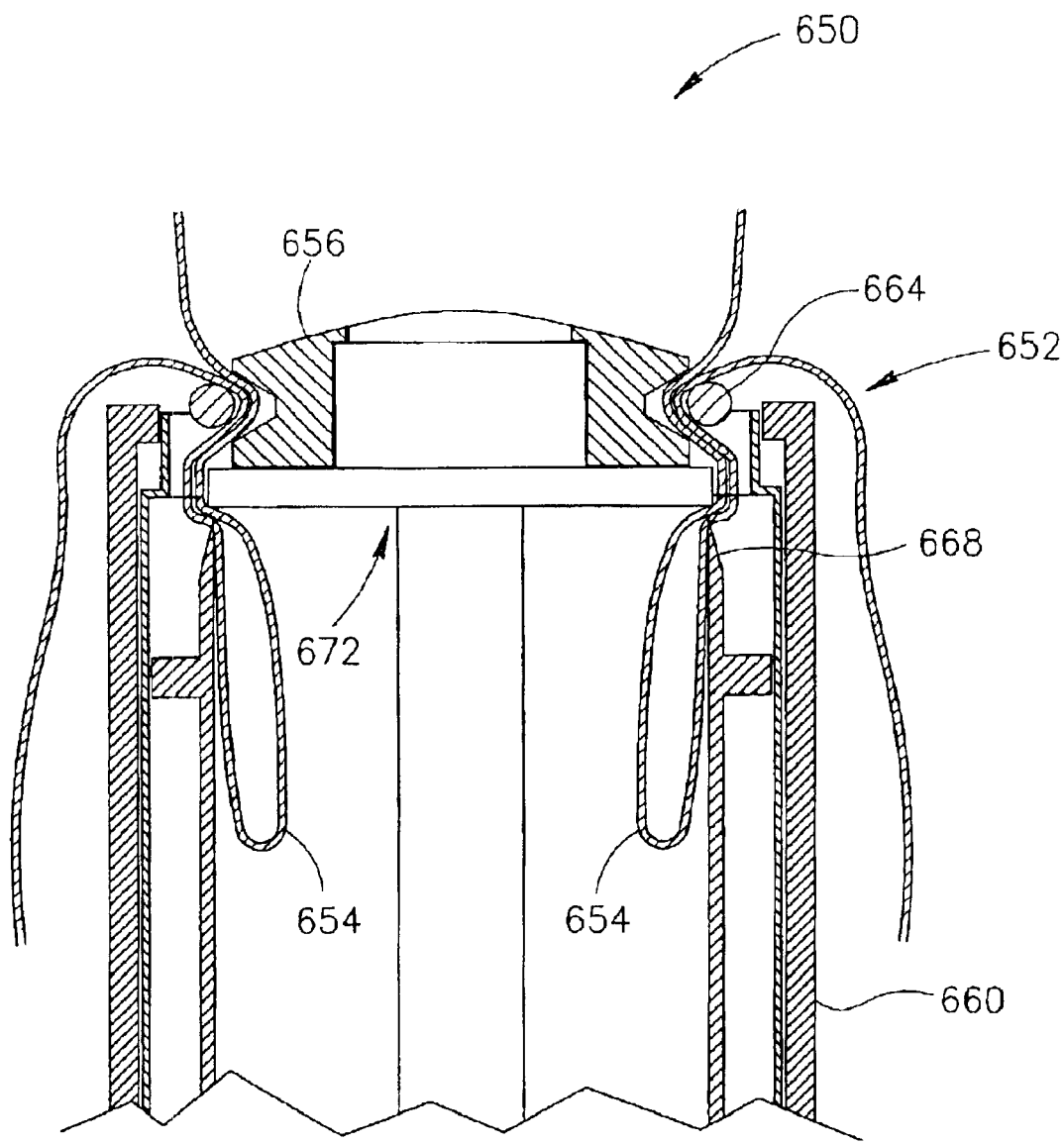
FIG. 28 illustrates anastomosis of the prolapsed bowel with a cylindrical cutting blade in cutting engagement therewith.

Referring now to FIGS. 27 and 28, there is seen an intratubular anastomosis apparatus generally referenced 650 inserted into a prolapsed bowel generally referenced 652 for bringing about anastomosis of organ referenced 652 followed by excising of prolapsed portion referenced 654. In FIG. 27 there is seen crimping support element referenced 656 proximally retracted to be brought into alignment with recess referenced 666 of crimping support element 656 in preparation for crimping prolapsed bowel portion 654 against crimping support element 656. Retraction of anastomosis ring applicator referenced 662, causes anastomosis ring referenced 664 to disengage from recess 666 and to crimp prolapsed organ portion 654 as seen in FIG. 28. Thereafter, cylindrical cutting blade referenced 668 is brought into cutting engagement with crimping support applicator referenced 672 thereby to excise prolapsed organ portion 654. Crimping support element 656 and anastomosis ring 664 are disengaged from crimping support applicator 672 (as disclosed hereinabove in relation to FIGS. 19–22) to provide patency to anastomosed organ 652.

It will, further, be appreciated by persons skilled in the art that there is a direct relationship between the size and thickness of the anastomosis ring and crimping support element used in the surgical procedure disclosed above and the size and shape of the organ to be treated. An anastomosis ring and crimping support element of a particular size is selected so as to achieve an aperture of a requisite size or situation, as appropriate to the hollow organ to be subjected to intussusception and anastomosis. Clearly, a smaller size is appropriate for use in the upper bowel and a larger size in the lower bowel.

Additionally, it will be appreciated by persons skilled in the art, that an apparatus employing a shape memory alloy, such as an anastomosis ring, referred to hereinabove according to embodiments of the present invention, may be described as being of one of two different types. A first type of apparatus employs a shape memory alloy, which is in an easily deformable, martensitic state when it is cooled to below room temperature, called a "Cold" type. This first apparatus achieves a fully or partial austenitic state at room temperature, and a completely austenitic state when heated to at least its upper phase transition temperature, between room and body temperature. In a second type of apparatus, the shape memory alloy is in an easily deformable, martensitic state at room temperature, called a "Hot" type, whereat the apparatus is deformed and applied, and the shape memory alloy achieves a completely austenitic state when heated to above room temperature. The temperature range over which the shape memory alloy is easily deformable defines the difference between the two types of apparatus. Thus, utilizing an apparatus including a shape memory alloy of the second Hot type allows more freedom in application without necessitating cooling below room temperature. The present invention disclosed hereinabove relates to a apparatus of the first Cold type, necessitating cooling below room temperature.

Considering the "Lot" type, in which the transformation temperature is higher, the clip is martensitic at room temperature and heated to about 42–45° C. to assume an austenitic state. When the temperature drops to 37° C., that is, body temperature, the martensitic transformation is not complete, leaving the clip in a transition state, with inferior mechanical characteristics.

It should be understand that the so-called transformation temperature of the alloy, in fact, is a process of transformation. Transition from a martensitic to an austenitic state starts at a temperature $A_s$ and ends with at temperature $A_f$ at which the state becomes fully austenitic. When transforming from austenitic to martensitic state, by dropping the temperature, the alloy starts to become martensitic at temperature $M_s$, and reaches a full martensitic state at temperature $M_f$.

In the Cold type, generally preferred in accordance with embodiments of the present invention, $A_f$ is lower than body temperature, generally about 25° C. In the Hot type, $M_f$ is below body temperature, so that the alloy does not become fully martensitic at body temperature.

It will be appreciated by persons skilled in the art that the present invention is not limited by the drawings and description hereinabove presented. Rather, the invention is defined solely by the claims that follow.

What is claimed is:

1. An intratubular anastomosis apparatus for joining organ portions of a hollow organ after intussusception thereof, said apparatus including:

a) an anastomosis ring, and b) a crimping support element for use therewith, wherein said anastomosis ring includes a length of a wire having a predetermined cross-sectional configuration and formed of a shape memory alloy defining a closed generally circular shape, having a central opening, and having overlapping end portions, said anastomosis ring for crimping adjacent organ portions against said crimping support element so as to cause anastomosis therebetween, wherein said anastomosis ring and said shape memory alloy assumes i) a plastic state, when at a first, lower temperature and ii) an elastic state, when reaching at least a second, higher temperature, thereby enabling said anastomosis ring to retain a preselected configuration at the first, lower temperature, and an elastic crimping configuration upon reverting to the second, higher temperature; and wherein said crimping support element for intratubular insertion so as to provide a support for crimping said organ portions against said support element, said crimping support element having i) a generally cylindrical side-wall;
ii) proximal and distal end walls formed generally transversely to said side-wall, thereby to define therewith said crimping support element,
iii) a generally axial aperture for providing flow communication therethrough, and
iv) attachment means for operationally engaging said crimping support element to a crimping applicator member so as to position said crimping support element adjacent to said anastomosis ring for facilitating crimping of preselected wall portions of a hollow organ therebetween.

2. An intratubular anastomosis apparatus according to claim 1, wherein said anastomosis ring is a contracting anastomosis ring at the second higher temperature.

3. An intratubular anastomosis apparatus according to claim 1, wherein said crimping support element has an circumferential recess formed in an outer surface thereof for facilitating retaining said contracting anastomosis ring in a predetermined position therein.

4. An intratubular anastomosis apparatus according to claim 1, wherein said proximal and distal end walls include at least one proximal and distal lug respectively for facilitating retaining said contracting anastomosis ring in a predetermined position therebetween.

5. For use with an anastomosis ring, a crimping support element arranged to have intussuscepted organ wall portions crimped thereagainst by the anastomosis ring, so as to cause anastomosis between the wall portions, wherein the anastomosis ring includes a length of a wire having a predetermined cross-sectional configuration and formed of a shape memory alloy defining a closed generally circular shape having a central opening and having overlapping end portions, for crimping adjacent intussuscepted organ wall portions, so as to cause anastomosis between the wall portions, and wherein said anastoniosis ring and said shape memory alloy assumes i) a plastic state, when at a first, lower temperature and
ii) an elastic state, when reaching at least a second, higher temperature, thereby enabling said anastomosis ring to retain a preselected configuration at the first, lower temperature, and an elastic crimping configuration upon reverting to the second, higher temperature, wherein said crimping support element includes:
a) a generally cylindrical side-wall;
b) proximal and distal end walls formed generally transversely to said side-wall, thereby to define therewith said crimping support element;
c) a generally axial aperture for providing flow communication therethrough; and d) attachment means for operationally engaging said crimping support element to a crimping applicator member so as to position said crimping support element adjacent to said anastomosis ring for facilitating crimping of preselected wall portions of a hollow organ therebetween.

6. For use with an anastomosis ring, a crimping support element according to claim 5, wherein said crimping support element has an circumferential recess formed in an outer surface thereof for facilitating retaining said contracting anastomosis ring in a predetermined position therein.

7. For use with an anastomosis ring, a crimping support element according to claim 5, wherein said proximal and distal end walls include at least one proximal and distal lug respectively for facilitating retaining said contracting anastomosis ring in a predetermined position therebetween.

8. An intratubular anastomosis apparatus for joining organ portions of a hollow organ after intussusception thereof, said apparatus including:

a) an anastomosis ring, and
b) a crimping support element for use therewith, wherein said anastomosis ring includes a length of a wire having a predetermined cross-sectional configuration and formed of a shape memory alloy defining a closed generally circular shape, having a central opening, and having overlapping end portions, said anastomosis ring for crimping adjacent organ portions against said crimping support element so as to cause anastomosis therebetween, wherein said anastomosis ring and said shape memory alloy assumes i) a plastic state, when at a first, lower temperature and
ii) an elastic state, when reaching at least a second, higher temperature, thereby enabling said anastomosis ring to retain a preselected configuration at the first, lower temperature, and an elastic crimping configuration upon reverting to the second, higher temperature; and wherein said crimping support element for intratubular insertion so as to provide a support for crimping said organ portions against said support element, said crimping support element having i) a generally cylindrical side-wall;
ii) proximal and distal end walls formed generally transversely to said side-wall, thereby to define therewith said crimping support element, and wherein said proximal and distal end walls include at least one proximal and distal lug respectively for facilitating retaining said contracting anastomosis ring in a predetermined position therebetween;
iii) a generally axial aperture for providing flow communication therethrough; and
iv) attachment means for operationally engaging said crimping support element to a crimping applicator member so as to position said crimping support element adjacent to said anastomosis ring for facilitating crimping of preselected wall portions of a hollow organ therebetween.

* * * * *